(12) United States Patent
Liu et al.

(10) Patent No.: US 8,725,238 B2
(45) Date of Patent: May 13, 2014

(54) ELECTROCARDIOGRAM SIGNAL PROCESSING SYSTEM

(75) Inventors: Xin Liu, Singapore (SG); Yuanjin Zheng, Singapore (SG); Myint Wai Phyu, Singapore (SG); Bin Zhao, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 682 days.

(21) Appl. No.: 12/878,800

(22) Filed: Sep. 9, 2010

(65) Prior Publication Data

US 2011/0077538 A1 Mar. 31, 2011

Related U.S. Application Data

(60) Provisional application No. 61/241,550, filed on Sep. 11, 2009.

(51) Int. Cl.
*A61B 5/0432* (2006.01)

(52) U.S. Cl.
USPC .......................................... 600/509; 600/523

(58) Field of Classification Search
USPC ......... 600/300, 301, 508, 509, 523, 512, 513; 607/27
See application file for complete search history.

(56) References Cited

U.S. PATENT DOCUMENTS

| | | |
|---|---|---|
| 5,778,881 A | 7/1998 | Sun et al. |
| 5,782,888 A | 7/1998 | Sun et al. |
| 6,184,942 B1 * | 2/2001 | Patel et al. ................... 348/726 |
| 6,970,737 B1 | 11/2005 | Brodnick et al. |
| 7,403,808 B2 | 7/2008 | Istvan et al. |
| 2004/0010203 A1 * | 1/2004 | Bibian et al. .................. 600/544 |
| 2006/0013473 A1 * | 1/2006 | Woodfill et al. .............. 382/154 |
| 2006/0200035 A1 * | 9/2006 | Ricci et al. .................... 600/513 |

FOREIGN PATENT DOCUMENTS

| | | |
|---|---|---|
| WO | 0182099 A1 | 11/2001 |
| WO | 2004089205 A1 | 10/2004 |
| WO | 2004095307 A2 | 11/2004 |
| WO | 2007131173 A2 | 11/2007 |
| WO | 2008014895 A1 | 2/2008 |

OTHER PUBLICATIONS

Adnane, M., et al., "Development of QRS Detection Algorithm Designed for Wearable Cardiorespiratory System", "Computer Methods and Programs in Biomed.", 2009, pp. 20-31, vol. 93, No. 1.

(Continued)

*Primary Examiner* — Eric D. Bertram
*Assistant Examiner* — Pamela M Bays
(74) *Attorney, Agent, or Firm* — Hultquist, PLLC; Steven J. Hultquist; Mary B. Grant

(57) ABSTRACT

An electrocardiogram signal processing system is provided which includes: a wavelet transformation unit comprising a plurality of outputs, each output being connected to one of a plurality of scales, wherein the wavelet transformation unit is adapted to transform an input electrocardiogram signal into a set of wavelets, each wavelet being output to one of the scales; a plurality of signal processing blocks, each of the signal processing blocks coupled to a respective output of the wavelet transformation unit and configured to receive and process the wavelet from the respective output, wherein the signal processing blocks provide processing functions which differ from one another.

30 Claims, 20 Drawing Sheets

(56) References Cited

OTHER PUBLICATIONS

Afonso, V.X., et al., "ECG Beat Detection Using Filter Banks", "IEEE Trans. Biomedical Engineering", 1999, pp. 192-202, vol. 46, No. 2.

Bahoura, M., et al., "DSP Implementation of Wavelet Transform for Real Time ECG Wave Forms Detection and Heart Rate Analysis", "Computers Methods and Programs in Biomedicine", 1997, pp. 35-44, vol. 52, No. 1.

Benitez, D.S., et al., "A New QRS Detection Algorithm Based on the Hilbert Transform", "Computers in Cardiology", 2000, pp. 379-382, vol. 27.

Benitez, D., et al., "The Use of the Hilbert Transform in ECG Signal Analysis", "Computers in Biology and Medicine", 2001, pp. 399-406, vol. 31, No. 5.

Crouse, M.S., et al., "Wavelet-Based Statistical Signal Processing Using Hidden Markov Models", "IEEE Trans. Signal Processing", 1998, pp. 886-902, vol. 46, No. 4.

(Author unknown), "ECG Signal Compression Using Analysis by Synthesis Coding", accessed online at http://researcher.nsc.gov.tw/public/8905780/Attachment/82261685771.pdf (undated).

Guo, D.G., et al., "A Wearable BSN-based ECG-recording System Using Micromachined Electrode for Continuous Arrhythmia Monitoring", "IEEE, Proceedings of 5th International Workshop on Wearable and Implantable Body Sensor Networks", 2008.

Hoang, T.T., et al., "A Low Complexity, Low Power, Programmable QRS Detector Based on Wavelet Transform for Implantable Pacemaker IC", IEEE, SOC Conference, 2006, pp. 160-163.

Kadambe, S., et al., "Wavelet Transform-Based QRS Complex Detector", "IEEE Trans. Biomedical Engineering", 1999, pp. 838-848, vol. 46, No. 7.

Köhler, B.U., et al., "The Principles of Software QRS Detection", "IEEE Engineering in Medicine and Biology Magazine", 2002, pp. 42-57, vol. 21, No. 1.

Kuon, I., et al., "Measuring the Gap between FPGAs and ASICs", "Int. Symp. on Field Programmable Gate Arrays", 2006, pp. 21-30.

Li, C., et al. "Detection of ECG Characteristic Points Using Wavelet Transforms", "IEEE Trans. Biomedical Engineering", 1995, pp. 21-28, vol. 42, No. 1.

Mallat, S., et al., "Characterization of Signals from Multiscale Edges", "IEEE Transactions on Pattern Analysis and Machine Intelligence", 1992, pp. 710-732, vol. 14, No. 7.

Mallat, S., et al., "Singularity Detection and Processing with Wavelets", "IEEE Trans. Inform. Theory", 1992, pp. 617-643, vol. 38, No. 2.

Martinez, J.P., et al., "A Wavelet-Based ECG Delineator: Evaluation on Standard Databases", "IEEE Trans. Biomed. Eng.", 2004, pp. 570-581, vol. 51, No. 4.

Nibouche, M., et al., "FPGA-Based Discrete Wavelet Transforms System", "Lecture Notes in Computer Science", 2001, pp. 607-612, vol. 2147.

Pan, J., et al., "A Real-Time QRS Detection Algorithm", "IEEE Trans. Biomedical Engineering", 1985, pp. 230-236, vol. 32, No. 3.

Poli, R., et al., "Genetic Design of Optimum Linear and Nonlinear QRS Detector", "IEEE Trans. Biomedical Engineering", 1995, pp. 1137-1141, vol. 42, No. 11.

Raj, C.P., "Design and Implementation of Parallel and Pipelinined Distributive Arithmetic Based Discrete Wavelet Transform IP Core", "Accessed online at http://www.design-reuse.com/articles/17024/design-and-implementation-of-parallel-and-pipelinined-distributive-arithmetic-based-discrete-wavelet-transform-ip-core.html", 2009.

Sadler, B.M., et al., "Analysis of Multiscale Products for Step Detection and Estimation", "IEEE Trans. Information Theory", 1999, pp. 1043-1051, vol. 45, No. 3.

German-Sallo, Z., "Applications of Wavelet Analysis in ECG Signal Processing", "Technical University of Cluj-Napoca; Summary of PhD Thesis", 2005.

Suarez K.V., et al., "ECG Beat Detection Using a Geometrical Matching Approach", "IEEE Trans. Biomedical Engineering", 2007, pp. 641-650, vol. 54, No. 4.

Thakor, N.V., et al., "Estimation of QRS Complex Power Spectra for Design of a QRS Filter", "IEEE Trans. Biomedical Engineering", 1984, pp. 702-706, vol. 31, No. 11.

Tseng, P., et al., "Generic RAM-Based Architecture for Two-Dimensional Discrete Wavelet Transform with Line-Based Method", "IEEE", 2002, pp. 363-366, vol. 1.

Vaessen, M.J., "A QRS Detection Method Using Analog Wavelet Transform in ECG Analysis", "Maastricht University; Bachelors' Thesis", 2005.

Xu, Y., et al., "Wavelet Transform Domain Filters: A Spatially Selective Noise Filtration Technique", "IEEE Trans. Image Processing", 1994, pp. 747-758, vol. 3, No. 6.

Xue, Q., et al., "Neural-Network-Based Adaptive Matched Filtering for QRS Detection", "IEEE Trans. Biomedical Engineering", 1992, pp. 317-329, vol. 39, No. 4.

Zheng, Y., et al., "Recursive Adaptive Algorithms for Fast and Rapidly Time-Varying Systems", "IEEE Trans. Circuits and Systems II: Analog and Digital Signal Processing", 2003, pp. 602-614, vol. 50, No. 9.

\* cited by examiner

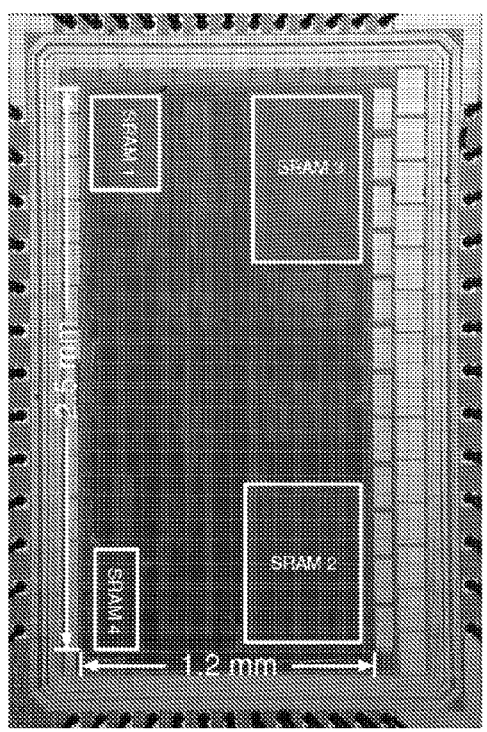

| Chip Specifications | |
|---|---|
| CMOS Process | 0.18 μm CMOS |
| Chip Area | 1.2x2.5 mm² |
| Number of standard cells | 48 kbits |
| Memory | SRAM 1: 14400 units; SRAM 2: 61440 units; SRAM 3: 56960 units; SRAM 4: 5680 units |
| Operation Frequency | 32 kHz for SRAM 1 kHz for others |
| Supply Voltage | 1 V |
| Power Consumption | 29 μW |
| I/O Specifications | |
| Input | 9 bits ECG signals |
| Output | 9 bits clean ECG signals 1 bit QRS peak 9 bits long-term HBR monitoring 9 bits short-term HBR monitoring |
| Key SoC Features | |
| Baseline drift removal | Adaptive filter order adjustment |
| QRS peak detection | >99.8% detection ratio |
| HBR prediction & classification | Long-term & short-term prediction for the individual status of different patients |
| Clean ECG reconstruction | Convenient for monitoring and diagnosis |

Figure 10B

TABLE I
THE PERFORMANCE OF THE ALGORITHM FOR THE MIT/BIH ARRHYTHMIA DATABASE

| record | TP | FP | FN | FP + FN | Se (%) | +P (%) |
|---|---|---|---|---|---|---|
| 100 | 2273 | 0 | 0 | 0 | 100.00 | 100.00 |
| 101 | 1865 | 0 | 2 | 2 | 99.89 | 100.00 |
| 102 | 2187 | 4 | 25 | 29 | 98.87 | 99.82 |
| 103 | 2084 | 0 | 1 | 1 | 99.95 | 100.00 |
| 104 | 2229 | 1 | 1 | 2 | 99.95 | 99.95 |
| 105 | 2572 | 16 | 31 | 47 | 98.81 | 99.38 |
| 106 | 2027 | 1 | 15 | 16 | 99.2 | 99.95 |
| 107 | 2137 | 2 | 12 | 14 | 99.5 | 99.91 |
| 108 | 1763 | 1 | 22 | 23 | 98.77 | 99.95 |
| 109 | 2532 | 0 | 0 | 0 | 100.00 | 100.00 |
| 111 | 2124 | 0 | 1 | 1 | 99.95 | 100.00 |
| 112 | 2539 | 0 | 2 | 2 | 99.91 | 100.00 |
| 113 | 1795 | 0 | 0 | 0 | 100.00 | 100.00 |
| 114 | 1879 | 0 | 1 | 0 | 99.95 | 100.00 |
| 115 | 1953 | 2 | 2 | 4 | 99.91 | 99.91 |
| 116 | 2412 | 12 | 2 | 14 | 99.91 | 99.5 |
| 117 | 1535 | 0 | 0 | 0 | 100.00 | 100.00 |
| 118 | 2275 | 0 | 8 | 8 | 99.65 | 100.00 |
| 119 | 1987 | 2 | 0 | 2 | 100.00 | 99.91 |
| 121 | 1863 | 0 | 1 | 1 | 99.95 | 100.00 |
| 122 | 2476 | 0 | 1 | 1 | 99.95 | 100.00 |
| 123 | 1518 | 0 | 2 | 2 | 99.91 | 100.00 |
| 124 | 1619 | 1 | 0 | 1 | 100.00 | 99.95 |
| 200 | 2601 | 24 | 5 | 29 | 99.81 | 99.08 |
| 201 | 1963 | 2 | 55 | 57 | 97.27 | 99.91 |
| 202 | 2136 | 0 | 11 | 11 | 99.49 | 100.00 |
| 203 | 2980 | 15 | 7 | 22 | 99.77 | 99.2 |
| 205 | 2656 | 0 | 2 | 0 | 99.91 | 100.00 |
| 207 | 1860 | 19 | 45 | 64 | 97.64 | 98.99 |
| 208 | 2955 | 1 | 129 | 130 | 95.82 | 99.95 |
| 209 | 3005 | 1 | 1 | 0 | 99.95 | 99.95 |
| 210 | 2650 | 1 | 29 | 30 | 98.92 | 99.95 |
| 212 | 2748 | 1 | 1 | 2 | 99.95 | 99.95 |
| 213 | 3251 | 0 | 5 | 5 | 99.84 | 100.00 |
| 214 | 2262 | 1 | 2 | 3 | 99.91 | 99.95 |
| 215 | 3363 | 0 | 1 | 1 | 99.95 | 100.00 |
| 217 | 2208 | 1 | 49 | 50 | 97.83 | 99.95 |
| 219 | 2154 | 0 | 3 | 3 | 99.86 | 100.00 |
| 220 | 2048 | 0 | 0 | 0 | 100.00 | 100.00 |
| 221 | 2427 | 4 | 4 | 8 | 99.84 | 99.84 |
| 222 | 2483 | 1 | 11 | 12 | 99.55 | 99.95 |
| 223 | 2605 | 0 | 4 | 4 | 99.85 | 100.00 |
| 228 | 2053 | 1 | 6 | 7 | 99.71 | 99.95 |
| 230 | 2256 | 0 | 0 | 0 | 100.00 | 100.00 |
| 231 | 1571 | 1 | 1 | 2 | 99.95 | 99.95 |
| 232 | 1780 | 0 | 0 | 0 | 100.00 | 100.00 |
| 233 | 3079 | 2 | 1 | 3 | 99.91 | 99.95 |
| 234 | 2753 | 0 | 0 | 0 | 100.00 | 100.00 |
| Total | 109291 | 117 | 500 | 617 | 99.63 | 99.89 |

Figure 18

ELECTROCARDIOGRAM SIGNAL PROCESSING SYSTEM

CROSS-REFERENCE TO RELATED APPLICATION

This application claims priority of U.S. Provisional Patent Application No. 61/241,550 filed on Sep. 11, 2009. The disclosure of the foregoing application is hereby incorporated herein by reference in its respective entirety, for all purposes.

TECHNICAL FIELD

Various embodiments relate to an electrocardiogram signal processing system.

BACKGROUND

Electrocardiogram (ECG) is the electrical representation of the contractile activity of the heart over time, which can be easily recorded using non-invasive electrodes on the chest or limbs. ECG indicates the overall rhythm of the heart and weaknesses in different parts of the heart muscle, and can measure and diagnose abnormal rhythms of the heart.

An ECG signal can be represented by a cyclic occurrence of patterns with different frequency content (QRS complexes, P and T waves). The different types of noise and interference can also be separated into different frequency bands.

Several well-documented signal processing algorithms exist that can separate an ECG signal into its different frequency bands. An example of a signal processing algorithm is wavelet transformation. Wavelet transform (WT) are mathematical functions that separate a signal into different frequency bands.

It is possible to apply different signal processing on different sub-bands to realize different functions. In known systems, for each of the different functions, a different signal processing algorithm is used to separate the ECG signal into its different frequency bands. This leads to an increase in the system size.

If many types of ECG signal processing can be integrated into one ASIC chip, the chip size can be quite small. There is thus a need to provide a compact ECG signal processing system which would be suitable for long-term monitoring

SUMMARY

According to an embodiment, an electrocardiogram signal processing system is provided. The electrocardiogram signal processing system includes: a wavelet transformation unit comprising a plurality of outputs, each output being connected to one of a plurality of scales, wherein the wavelet transformation unit is adapted to transform an input electrocardiogram signal into a set of wavelets, each wavelet being output to one of the scales; a plurality of signal processing blocks, each of the signal processing blocks coupled to some respective outputs of the wavelet transformation unit and configured to receive and process the wavelet from the respective output, wherein the signal processing blocks provide processing functions which differ from one another.

In the context of various embodiments, the term "electrocardiogram signal processing system" may mean an application specific integrated circuitry (ASIC) entirely fabricated on a single chip, in the context of semiconductor technology. The ASIC may have one or more devices that provide processing functions such as AND, NAND, or OR logic using transistors, resistors, capacitors, inductors and the like. Each of the one or more elements may serve any purpose, for example serving to perform wavelet transformation.

In the context of various embodiments, the term "wavelet transformation unit" may mean a device configured to perform wavelet transformation, which are mathematical functions that separate a signal into different frequency bands. In various embodiments, after the wavelet transformation, the signal is decomposed into a set of wavelets, with each wavelet having a respective frequency band.

In the context of various embodiments, the term "scale" may mean a port or signal path reserved to transmit signals of a designated bandwidth. In various embodiments, each scale may have a different bandwidth, wherein the wavelet output to one of the scales is derived from the wavelet output to an earlier scale. There may be at least eight scales, the scales having 3 dB bandwidths of around 250 to 500 Hz; 72 to 234 Hz; 32 to 108 Hz; 16 to 54 Hz; 8 to 26 Hz; 4 to 13 Hz; 2 to 6.5 Hz; and 1 to 3.25 Hz each, when the sampling rate of the input signal is 1 kHz.

In various embodiments, having the signal processing blocks configured to provide processing functions which differ from one another allows the electrocardiogram signal processing system to perform multiple functions on different scales. For instance, for the first to the fourth scales, signal processing blocks, where each provides noise suppression, QRS detection and HBR (heart beat rate) classification may be provided. For the fifth to the six scales, a signal processing block that provides data compression may be provided. For the seventh to the eight scales, signal processing blocks, where each provides data compression and baseline removal may be provided.

In the context of various embodiments, the term "configured" may mean that the signal processing blocks are each provided with electronics that are designed to process the wavelets from the output of the wavelet transformation unit connected thereto.

In various embodiments, the wavelet transformation unit may include a plurality of low pass filters and a plurality of high pass filters. The low pass filter for the first scale may be given by the expression $$l_{D,1}(k) = \frac{1}{8}\{\delta(k+2)+3\delta(k+1)+3\delta(k)+\delta(k-1)\}$$

and the high pass filter for the first scale may be given by the expression $$h_{D,1}(k) = 2\{\delta(k+1)-\delta(k)\},$$

wherein $\delta(k)$ is the Kronecker delta function and for scale numbers $n>1$, $l_{D,n}(k)$ and $h_{D,n}(k)$ are obtained by inserting $2^{n-1}-1$ zeros between each of the non-zero coefficients of $l_{D,1}(k)$ and $h_{D,1}(k)$.

In various embodiments, the low pass filters and the high pass filters have a cascaded arrangement, wherein an output of at least one of the low pass filters is coupled to an input of at least one of the high pass filters.

In various embodiments, the wavelet transformation unit may include a first memory array to achieve delay, the first memory array coupled to the last low pass filter of the cascaded chain of high pass filters and low pass filters.

In various embodiments, the signal processing blocks may include at least one wavelet denoising unit, an electrocardiogram signal reconstruction block, a data compression block, a baseline drift removal unit, a QRS detection unit and a HBR analysis unit. In various embodiments, having each signal processing block coupled to a respective output of the wavelet transformation unit allows each signal processing block to receive output of wavelets having a respective scale.

In various embodiments, the wavelet denoising unit may suppress high frequency noise and may be coupled to one of the respective outputs of the wavelet transforming unit emitting wavelets coupled to the first three scales and wherein the suppressed high frequency noise falls in a range of above 32 Hz.

In various embodiments, the electrocardiogram signal reconstruction block may process wavelets belonging to the first to the eighth scales and may reconstruct an ECG signal from the plurality of wavelets from the first to the eighth scales. Compared to the ECG signal input into the wavelet transformation unit, the reconstructed ECG signal is cleaner in that it has been processed to remove noise and baseline drifting. In various embodiments, the electrocardiogram signal reconstruction block further may include a first reconstruction block for the fifth to the eighth scales; a second reconstruction block for the first to the fourth scales; and a third reconstruction block for the first to the eighth scales.

In one embodiment, the first reconstruction block, the second reconstruction block and the third reconstruction block may include shift registers to achieve delay. In another embodiment, the first reconstruction block, the second reconstruction block and the third reconstruction block may include memory arrays to achieve delay. In a further embodiment, the first reconstruction block, the second reconstruction block and the third reconstruction block may include both shift registers and memory arrays to achieve delay.

In various embodiments, SRAM may be used for the memory arrays.

In various embodiments, the first reconstruction block may output synchronized signals belonging to the high-pass filtered components of the fifth to the eighth scales; the second reconstruction block may output synchronized signals belonging to the high-pass filtered components of the first to the fourth scales; and the third reconstruction block may output signals belonging to the low-pass filtered components of the first to the seventh scales. The output of the first to the third reconstruction blocks may be a reconstructed electrocardiogram signal.

In various embodiments, the second reconstruction block may be coupled to an output of one of the at least one wavelet denoising unit to receive denoised wavelets belonging to the first to the third scales.

In various embodiments, the data compression block may receive wavelets of the fifth to the eighth scales, wherein an output of the data compression block is coupled to the input of the first reconstruction block.

In various embodiments, the data compression block may be realized using finite-impulse-response filters and infinite-impulse-response filters, wherein either filter compensates poles and zeros of the other filter.

In various embodiments, the baseline drift removal unit may be coupled to the respective output of the wavelet transforming unit emitting wavelets belonging to the seventh and the eighth scales.

In various embodiments, the baseline drift removal block may be realized by an adaptive cascaded filter arrangement, the cascaded filter arrangement comprising at least one filter stage. In various embodiments, the adaptive cascaded filter arrangement may automatically switch off filter stages unnecessary for performing baseline drift removal. The unnecessary filter stages may be those larger than a filter stage in which the difference in the output value of the filter stage and an output value of the largest filter stage is smaller than a specified threshold. In various embodiments, the adaptive cascaded filter arrangement may include chebyshev IIR filters.

In various embodiments, the QRS detection unit may be coupled to the output of the at least one wavelet denoising unit and the output of the wavelet transforming unit emitting wavelets belonging to the fourth scale. The QRS detection unit may include a wavelet summation unit to sum the denoised wavelets from the at least one wavelet denoising unit and the wavelets from the wavelet transforming unit, wherein QRS peaks are detected when the summed wavelets exceed an adaptive threshold value.

In various embodiments, the QRS detection unit may be realized using any of a Field Programmable Gate Array (FPGA), Application Specific Integrated Circuits (ASIC) or be implemented by software. In various embodiments, the wavelet summation unit may include an adder; and the QRS peaks may be detected using a subtractor and multiplexer. The adaptive threshold value may be derived from a standard deviation of a number of sampled summed wavelets.

In various embodiments, the HBR analysis unit may be coupled to an output of the QRS detection unit. In various embodiments, the HBR analysis unit may include a counter; two multiplication modules; an adder and a delay block. In various embodiments, the HBR analysis unit may be realized by a Field Programmable Gate Array (FPGA), Application Specific Integrated Circuits (ASIC) or be implemented by software. In various embodiments, the HBR analysis unit may be adapted to predict QRS peak intervals based on a forward prediction algorithm. The forward prediction algorithm may be based on summing previous QRS peak intervals weighted with a forgetting factor, the forgetting factor determining the number of previous QRS peak intervals included for HBR analysis.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 10B shows a die photo of a fabricated electrocardiogram signal processing system according to an embodiment.

FIG. 18 shows a table summarising obtained QRS detection results of the chip of FIG. 13.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

To achieve high power & area efficiency, embodiments of an electrocardiogram signal processing system use wavelet transform (WT) algorithm to integrate multiple functions. Embodiments of the electrocardiogram signal processing system provide a dedicated power & area efficient non-downsampling WT ASIC implementation structure. WT separates incoming noisy ECG signals into different scales with different bandwidth. Consequently, high frequency noise is suppressed by a de-noising block on the outputs of non-downsampling WT decomposition (NDWTD) scales 1 to 3. A real-time adaptive QRS detection block uses the de-noised NDWTD outputs to acquire the QRS peaks. The HBR prediction and classification is performed by a prediction & classification block. The artificial baseline drift is suppressed by a baseline drift removal block on the outputs of NDWTD scales 7 to 8. After removing high-frequency noise components and the low-frequency baseline drift, the clean ECG signal can be reconstructed by a nondownsampling WT reconstruction (NDWTR) block. All blocks may communicate with each other in 1 kHz frequency.

Figure 1:
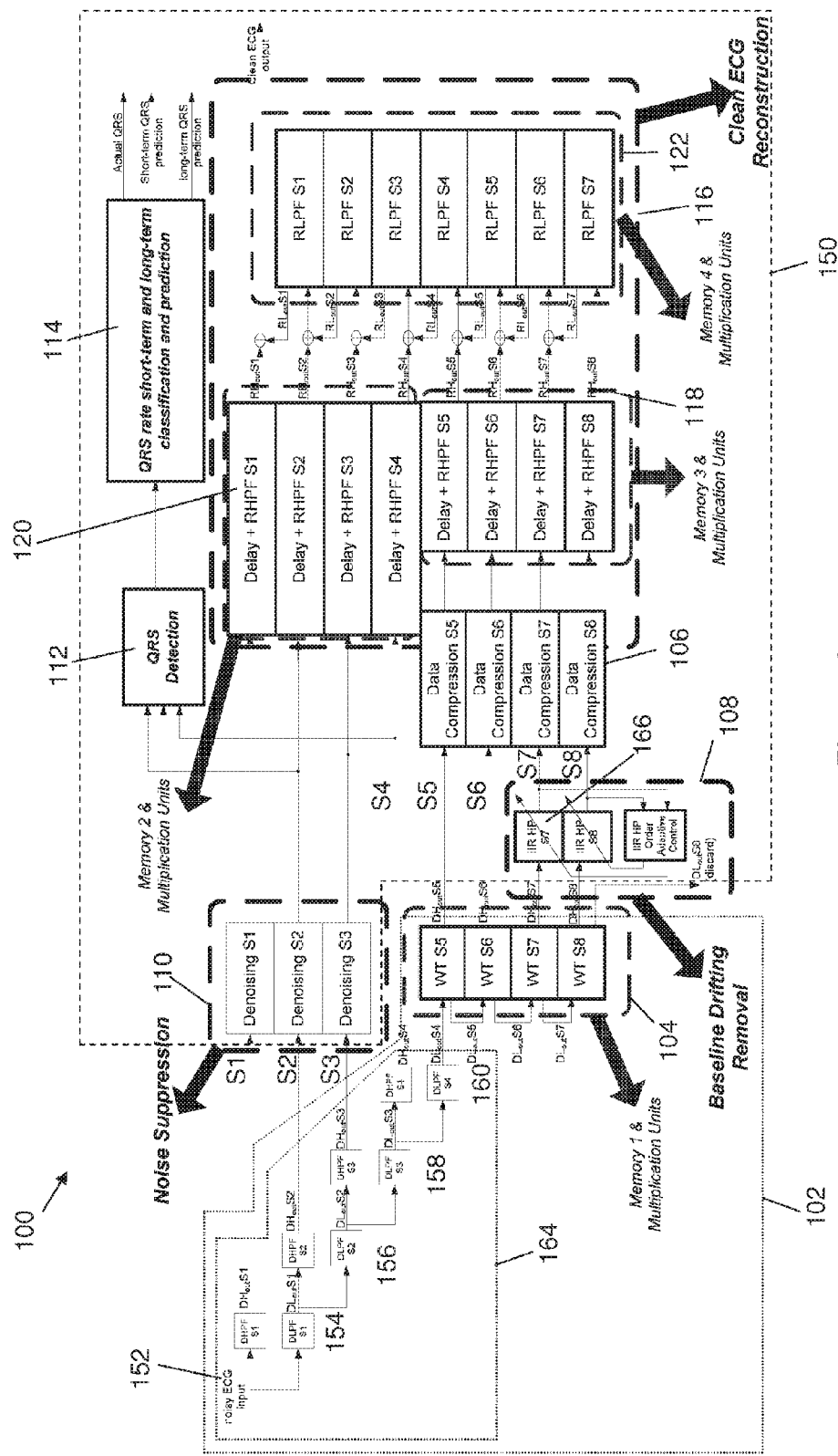
FIG. 1 shows the architecture of an electrocardiogram signal processing system built according to one embodiment.

FIG. 1 shows the architecture of an electrocardiogram signal processing system 100 built according to one embodiment. In the embodiment shown in FIG. 1, the electrocardiogram signal processing system 100 may be entirely fabricated on a single chip.

An overview of the electrocardiogram signal processing system 100 is as follows. A signal acquisition front-end circuit provides 9-bits digitalized ECG signals 152 to the electrocardiogram signal processing system 100 with $f_1=1$ kHz sampling rate. The same sampling rate may be maintained in different WT scales S1 to S8 to avoid the issues of time-shifting and the temporal resolution degradation, as reported in J. P. Martìnez, R. Almeida, S. Olmos, A. P. Rocha, and P. Laguna, "A wavelet-based ECG delineator: evaluation on standard databases," *IEEE Trans. Biomedical Engineering*, vol. 51, no. 4, pp. 570-581, 2004. However, increasing the number of scales causes huge number of taps of WT low-pass filters (LPFs) and high-pass filters (HPFs). To optimize hardware implementation, a dedicated NDWT ASIC implementation structure is used. For scales 1~4 of NDWTD, since the total number of filter taps is small, conventional shift registers based FIR filter structure may be used with the operation clock being $f_1=1$ kHz. Subsequently, 4 single-port static random access memories (SRAM1~4) may be used to realize the huge number of finite impulse response (FIR) filter taps and buffers between decomposition HPFs (DHPFs) and reconstruction HPFs (RHPFs). SRAM 1~4 are designed for scales 5~8 DLPFs and DHPFs, scales 1~4 RHPFs, scales 5~8 RHPFs, and scales 1~8 reconstruction LPFs (RLPFs), respectively. The operation of SRAM is time-division multiplexing (TDM), and its operation clock $f_2$ is 32 kHz. During one clock cycle of $f_1$, each SRAM writes and reads with sequential specific address and scale by scale with frequency $f_2$, which is higher than $f_1$. For each SRAM, only one multiplication module is required because of TDM. A control module for the SRAM generates control signals and controls a first multiplexer MUX1 to select signals from different scales and controls a second multiplexer MUX2 to select different multiplication factors for the outputs of different scales. Memory-based structure is used for the non-downsampling WT because of the large number of delays and small number of non-zero filter coefficients. Since memory based WT structure is simpler and smaller in layout, and no buffers need to be inserted for timing routing during place & route, the electrocardiogram signal processing system 100 may result in 55% area reduction over conventional shift register based structure.

The electrocardiogram signal processing system 100 includes: a wavelet transformation unit 102 and a plurality of signal processing blocks 150.

The plurality of signal processing blocks 150 includes a noise suppression block 110 (having at least one wavelet denoising unit), an electrocardiogram signal reconstruction block 116, a data compression block 106, a baseline drift removal unit 108, a QRS detection unit 112 and a HBR (heart beat rate) analysis unit 114. Each signal processing block (110, 116, 106, 108, 112 and 114) is coupled to a respective output of the wavelet transformation unit 102, which allows each signal processing block to receive input of wavelets having a respective scale. Thus, each signal processing block (110, 116, 106, 108, 112 and 114) is configured to receive and process the wavelet from the respective output. Each signal processing block (110, 116, 106, 108, 112 and 114) provides processing functions which differ from one another, allowing the electrocardiogram signal processing system 100 to perform multiple functions on the different scales S1 to S8. For instance, noise suppression, QRS detection and HBR classification may be performed on the first to the fourth scales S1 to S4. For the fifth to the six scales, data compression may be performed. For the seventh to the eight scales, data compression and baseline removal may be provided. By having each signal processing block (110, 116, 106, 108, 112 and 114) provide a different processing function, multiple functions are performable from the same generic output from the wavelet transformation unit 102.

Further detail on the wavelet transformation unit 102 and the plurality of signal processing blocks 150 is provided below.

The wavelet transformation unit 102 decomposes an input signal electrocardiogram signal 152 into different scales with different bandwidth. The quadratic spline wavelet function is normally used for ECG signal analysis.

The wavelet transformation unit 102 includes a plurality of outputs ($DH_{out}S1$, $DL_{out}S1$; $DH_{out}S2$, $DL_{out}S2$; $DH_{out}S3$, $DL_{out}S3$; $DH_{out}S4$, $DL_{out}S4$; $DH_{out}S5$, $DL_{out}S5$; $DH_{out}S6$, $DL_{out}S6$; $DH_{out}S7$, $DL_{out}S7$; $DH_{out}S8$, $DL_{out}S8$) of the outputs is connected to a respective one of a plurality of scales, S1 to S8. In the embodiment shown in FIG. 1, each of the scales S1 to S8 may be a port or signal path reserved to transmit signals of a designated bandwidth.

The wavelet transformation unit 102 is adapted to transform an input electrocardiogram signal 152 into a set of wavelets (being, in the embodiment shown in FIG. 1, a signal of a particular frequency band), each wavelet being output to one of the scales S1 to S8. There are thus at least eight scales, the scales having 3 dB bandwidths of around 250 to 500 Hz; 72 to 234 Hz; 32 to 108 Hz; 16 to 54 Hz; 8 to 26 Hz; 4 to 13 Hz; 2 to 6.5 Hz; and 1 to 3.25 Hz each, when the sampling rate of input signal is 1 kHz. These eight scales represent different characteristics of an ECG signal in different bandwidth.

In the embodiment shown in FIG. 1, the wavelet transformation unit 102 includes a filter arrangement 164. The filter arrangement 164 includes a plurality of low pass filters (154DLPF_S1, 156DLPF_S2, 158DLPF_S3, 160DLPF_S4) and a plurality of high pass filters (154DHPF_S1, 156DHPF_S2, 158DHPF_S3, 160DHPF_S4). Each high and low pass filter pair (154DHPF_S1, 154DLPF_S1; 156DHPF_S2, 156DLPF_S2; 158DHPF_S3, 158DLPF_S3; and 160DHPF_S4, 160DLPF_S4) are arranged in cascaded stages, whereby the input to each high and low pass filter pair (for instance 156DHPF_S2 and 156DLPF_S2) is from the output of the low pass filter (154DLPF_S1) of an earlier high and low pass filter pair (154DHPF_S1 and 154DLPF_S1). The output ($DH_{out}S1$, $DH_{out}S2$, $DH_{out}S3$, $DH_{out}S4$) from the high pass filters (154DHPF_S1, 156DHPF_S2, 158DHPF_S3, 160DHPF_S4) are connected to the scales S1 to S4. In this manner, the wavelet output to the scales S2, S3 and S4 is derived from the wavelet output to an earlier scale S1, S2 and S3 respectively, wherein each of the scales S1 to S4 has a different bandwidth.

In the embodiment shown in FIG. 1, the wavelet transformation unit 102 also includes a memory array 104 coupled to the filter arrangement 164. The memory array 104 includes several memory arrangements WT S5, WT S6, WT S7 and WT S8, each producing output of high frequency ($DH_{out}S5$, $DH_{out}S6$, $DH_{out}S7$, $DH_{out}S8$) and low frequency ($DL_{out}S5$, $DL_{out}S6$, $DL_{out}S7$, $DL_{out}S8$). The first memory arrangement WT S5 is coupled to the last low pass filter 160DLPF_S4 of the cascaded chain of high pass filters and low pass filters (154DHPF_S1, 154DLPF_S1; 156DHPF_S2, 156DLPF_S2; 158DHPF_S3, 158DLPF_S3; and 160DHPF_S4, 160DLPF_S4). Similar to the filter arrangement 164, the memory array 104 has a cascaded arrangement, whereby the input to each memory arrangement (for instance WT S6) is the low frequency output of an earlier memory arrangement (WT S5). The high frequency output ($DH_{out}S5$, $DH_{out}S6$, $DH_{out}S7$ and, $DH_{out}S8$) from the memory arrangements WT S5, WT S6, WT S7 and WT S8 are connected to the scales S5 to S8. In this manner, the wavelet output to the scales S5, S6, S7 and S8 is derived from the wavelet output to an earlier scale S4, S5, S6 and S7 respectively, wherein each of the scales S5 to S8 has a different bandwidth.

I Real-time Wavelet Transformation Unit and Electrocardiogram Signal Reconstruction Block; and Data Compression and Decompression Block A) Real-time Wavelet Transformation Unit and Electrocardiogram Signal Reconstruction Block As shown in FIG. 1, an ECG signal 152 is input into the wavelet transformation unit 102. Finite impulse response (FIR) filters may be used for the plurality of low pass filters (LPF) 154DLPF_S1, 156DLPF_S2, 158DLPF_S3 and 160DLPF_S4; and the plurality of high pass filters 154DHPF_S1, 156DHPF_S2, 158DHPF_S3 and 160DHPF_S4. The outputs of these filters can be down-sampled for removing the redundancy of the signal representation. However, the down-sampling procedure involves time-shifting for the signal representation, and reduces the temporal resolution of the wavelet coefficients when scales increase. To avoid time-shifting and resolution degradation issues, the same sampling rate in all scales is applied. In the decomposition part, for scale n, the outputs of decomposition LPF (DLPF) $y_n(i)$ and decomposition HPF (DHPF) $x_n(i)$ are given by $$y_n(i) = \sum_k l_{D,n}(k) y_{n-1}(i-k) \quad (1)$$

$$x_n(i) = \sum_k h_{D,n}(k) y_{n-1}(i-k) \quad (2)$$

respectively, where $Y_{n-1}(i)$ is the output of DLPF from scale n–1, $l_{D,n}(k)$ and $h_{D,n}(k)$ are the coefficients of DLPF and DHPF of scale n, respectively. For the first scale S1, $l_{D,1}(k)$ and $h_{D,1}(k)$ are given by $$l_{D,1}(k) = \frac{1}{8}\{\delta(k+2) + 3\delta(k+1) + 3\delta(k) + \delta(k-1)\} \quad (3)$$

$$h_{D,1}(k) = 2\{\delta(k+1) - \delta(k)\} \quad (4)$$

wherein $\delta(k)$ is the Kronecker delta function. For scale n>1, $l_{D,n}(k)$ and $h_{D,n}(k)$ are obtained by inserting $2^{n-1}-1$ zeros between each of the non-zero coefficients of $l_{D,1}(k)$ and $h_{D,1}(k)$.

In the electrocardiogram signal reconstruction block 116, an inverse wavelet transform (IWT) can reconstruct the signal from different scales. The reconstruction algorithm can be derived by $$w_n(i) = \sum_k l_{R,n}(k) w_{n+1}(i-k) + \sum_k h_{R,n}(k) x_{n+1}(i-k) \quad (5)$$

where $w_n(i)$, $l_{R,n}(k)$ and $h_{R,n}(k)$ are the outputs, coefficients of reconstruction LPF (RLPF) and coefficients of reconstruction HPF (RHPF) at scale n, respectively. For scale 1, $l_{R,1}(k)$ and $h_{R,1}(k)$ are expressed by $$l_{R,1}(k) = \frac{1}{8}\{\delta(k+2) + 3\delta(k+1) + 3\delta(k) + \delta(k-1)\} \quad (6)$$

$$h_{R,1}(k) = -0.0078125\delta(k+2) - 0.054685\delta(k+1) - 0.171875\delta(k) + 0.171875\delta(k-1) + 0.054685\delta(k-2) + 0.0078125\delta(k-3) \quad (7)$$

respectively. For scales n>1, $l_{R,n}(k)$ and $h_{R,n}(k)$ are obtained by inserting $2^{n-1}-1$ zeros between each of the non-zero coefficients of $l_{R,1}(k)$ and $h_{R,1}(k)$. The real-time wavelet transform occurring in various embodiments does not need to consider border problems, since the ECG signal 152 continuously inputs, so that only the initial several reconstructed ECG signal samples suffer distortion.

From equations (3), (4), (6) and (7), it can be observed that, for higher scale WT/IWT, the number of taps of LPFs and HPFs increase. For example when n=8, the number of taps of $l_{D,8}(k)$, $h_{D,8}(k)$, $l_{R,8}(k)$, and $h_{R,8}(k)$ becomes 385, 129, 385, and 641 respectively. Therefore, there will be a huge hardware cost for non-downsampling wavelet transformation low-pass and high-pass filtering.

When decomposing the ECG signal 152, the first scale S1 is first obtained, followed by the second scale S2, until the $N^{th}$ scale is finally obtained, which in the embodiment shown in FIG. 1 is the eighth scale S8. On the contrary, reconstruction is performed starting from the $N^{th}$ (being the eighth in the embodiment shown in FIG. 1) scale, then the $(N-1)^{th}$ (being the seventh in the embodiment shown in FIG. 1) scale and finally the first scale S1.

Therefore, for complete real-time wavelet transformation based decomposition and reconstruction, the delay between obtaining output of the first scale S1 from the DHPF before being processed by the RHPF for the first scale 51 for reconstruction is longest. On the other hand, the delay between obtaining output of the eighth scale S8 from the DHPF before being processed by the RHPF for the first scale S8 for reconstruction is shortest. Therefore, there are different processing delays for different scales.

Figure 2:
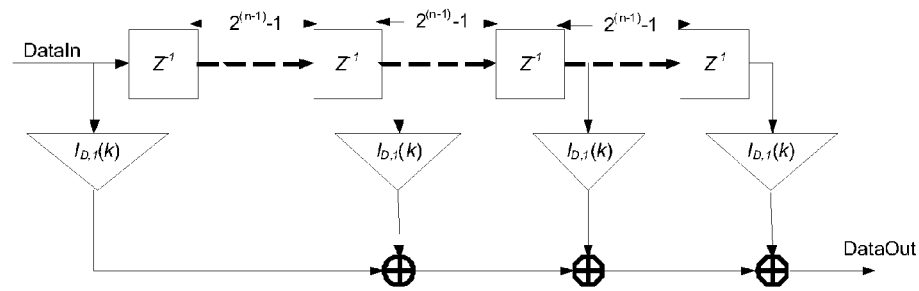
FIG. 2 shows shift register architecture.

For ASIC implementation of real-time signal processing, delays in a FIR filter may be implemented by shift registers. FIG. 2 shows DLPF implemented by shift register architecture 200 having shift registers 202, 204, 206 and 208. When new input data 210 enters, all data in a present register (for instance 202) is shifted to the next register (for instance 204).

For non-downsampling wavelet transformation HPFs and LPFs, the number of delays would be large, especially for higher scales. Further, to synchronize the DHPF outputs at the signal reconstruction block 116 (see FIG. 1) for different scales, a huge number of restore units have to be implemented, especially for the lower level. For example, the required delay for the scale S1 is 769.

Using Chartered 0.18 μm technology, one register occupies about 60 μm². On the contrary, the SRAM unit has comparatively simpler structure. To realize the large delay required by embodiments of the present invention, a large number of shift registers are needed, thus using the architecture shown in FIG. 2 would take up a large area.

In the interest of achieving a more compact device, delay may also be implemented by using static random access memory (SRAM).

Using single-port SRAM with the same technology to build 720×20 units and taking the area of I/O port into consideration, the average area for one unit is only about 8 μm², which is much smaller than that of the register.

A comparison between using shift registers and SRAM to achieve delay is provided below.

Every clock cycle of $f_1$, data stored in one register (for example 202) will shift to the next register (204), and thus the transition of register input will consume comparatively high power, especially when the chain of shifting registers is long. On the contrary, an SRAM need only write the data into a unit at a specific clock cycle and keep it, and then read the data out at another specific clock cycle. Therefore, power consumption by the SRAM is much lower than the shift registers.

A shift register needs to build clock tree to solve setup and hold time violation, and thus a large number of buffers need to be inserted between shift registers. These buffers result not only in a larger area, but also higher power consumption.

Time has also to be expanded on floorplan and routing when a large number of registers are used. Since, SRAM are already integrated, there is no requirement to consider how to place and perform internal routing. Thus, the SRAM provides a comparatively simpler structure.

According to equations (3), (4), (6) and (7), although the number of taps for HPFs and LPFs are huge, which is larger than $2^{n-1}-1$, the number of non-zero coefficient B is invariant for different scales. B=4 for $l_{D,n}(k)$ and $l_{R,n}(k)$, 2 for $h_{D,n}(k)$, and 6 for $h_{R,n}(k)$, which are quite small. It means that for each scale, only a few mathematical operations, including multiplication and addition, need to be executed on the data to be processed. The non-zero coefficients for different scales are the same as shown in equations (3), (4), (6), and (7). Therefore, the non-downsampling WT & IWT filters have "sparse" structures. For the scales S1 to S4 of WT decomposition, the total number of filter taps is not significantly large, therefore the shift register architecture 200 may be used to implement the filter arrangement 164, where the operation clock is the sampling rate of input signal $f_1$.

For the scales S5 to S8 (see FIG. 1), since the total number of filter taps is comparatively large, SRAM may be used instead of shift registers to realize the required delay. For scale n, the data from scale n−1 are continuously written into SRAM with continuous address. The data inside SRAM are read out with specific addresses to perform the operation of multiplication and addition.

Figure 3:
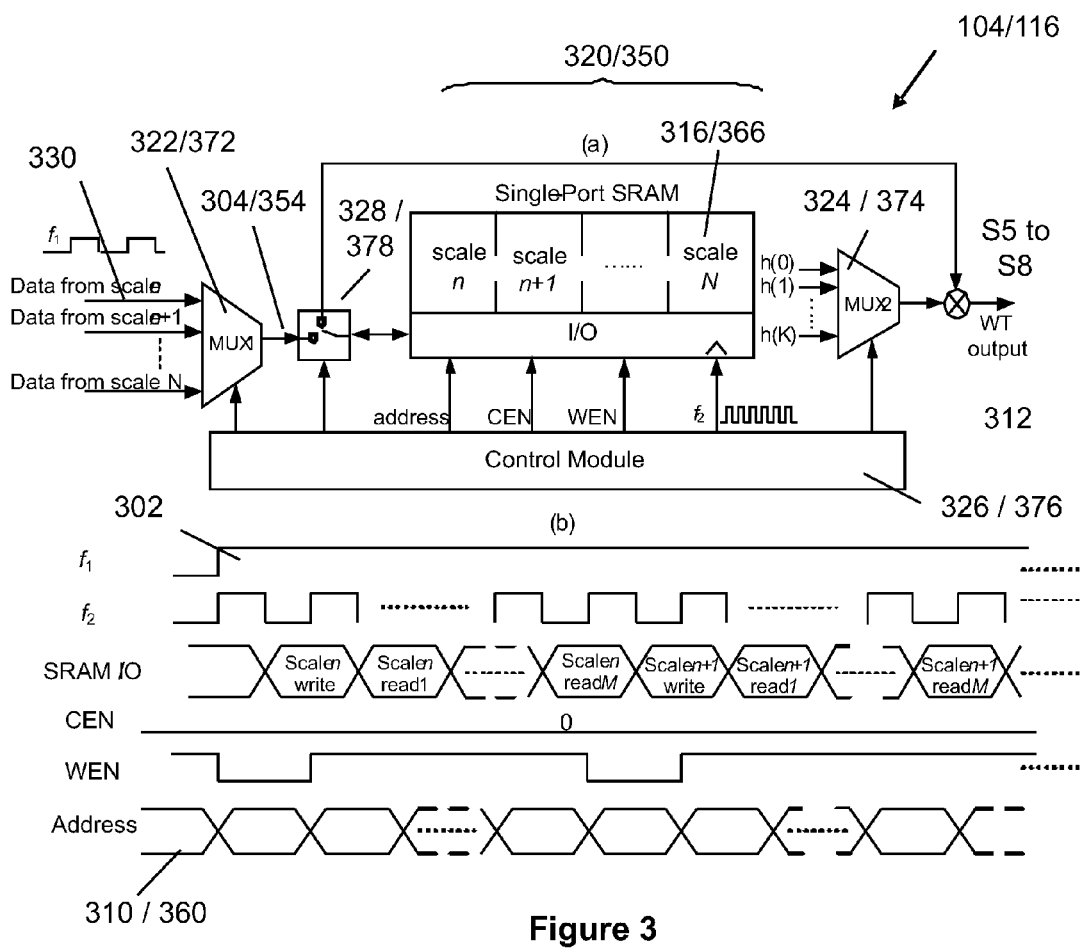
FIG. 3 shows a block diagram of a memory array.

FIG. 3 shows a block diagram of the memory array 104 of the wavelet transformation unit 102 (see FIG. 1). The memory array 104 has a SRAM array 320 having one or more single-port SRAM units 316. The memory array 104 includes a first multiplexer 322, a second multiplexer 324, a switch 328 and a control module 326. Similarly, the electrocardiogram signal reconstruction block 116 of the electrocardiogram signal processing system 100 (see FIG. 1) uses the same architecture shown in FIG. 3, whereby the electrocardiogram signal reconstruction block 116 has a SRAM array 350 having one or more single-port SRAM units 366. The electrocardiogram signal reconstruction block 116 includes a first multiplexer 372, a second multiplexer 374, a switch 378 and a control module 376.

First considering the decomposition of an ECG signal, since the sampling rate of input is $f_1$, the memory array 104 needs to operate at a higher operation frequency $f_2$. During one clock cycle 302 of $f_1$, one data sample 304 (containing data from output $DL_{out}S4$ of the last low pass filter 160DLPF_S4 of the filter arrangement 164 [see FIG. 1], or any one of the low-pass output $DL_{out}S5 \sim DL_{out}S7$ [also see FIG. 1] from an earlier operation of the memory array 104 itself) is written in through the switch 328. Data in the SRAM array 320 is also read out through the switch 328, containing four data samples, in accordance with equation (3), for calculating the output of DLPF (being the output $DL_{out}S5$, $DL_{out}S6$, $DL_{out}S7$ and $DL_{out}S8$; also see FIG. 1) and two data samples, in accordance with equation (4), for calculating the output of DHPF, using operation clock $f_2$. For each scale S5 to S8, the address 310 for writing data is cyclic shifting, so that the input data 304 can be sequentially written into the SRAM array 320. The addresses 310 for reading data are also cyclic shifting, and the difference between each address for reading is $2^{n-1}-1$, so that the data with different delay can be read out and multiplication performed at a multiplication module 312. Since the number of taps for DLPF is about two times of that of DHPF according to equations (3) and (4), the number of memory units is equal to the total taps of DLPF, which can satisfy both DLPF and DHPF, and thus one memory can be shared by both HPF and LPF for the same scale n. According to equations (1) and (2), the input data for both DLPF and DHPF is $y_{n-1}(i)$, and the delays of non-zero coefficient for DHPF are same as that of the middle two non-zero coefficient for DLPF. Assuming that data samples are termed D1~D4, according to equation (3), data samples D1, D2, D3, and D4 are needed to calculate DLPF, while according to equation (4), data samples D2, D3 are needed to calculate DHPF. Therefore, DHPF can share the same input as DLPF (being D2 and D3), i.e. the input data for both DLPF and DHPF can share the same address for reading data, and thus only four sets of data samples need to be read out for calculating outputs of both DLPF and DHPF, the four outputs of DHPF forming scales S5 to S8.

For wavelet reconstruction since the input data 354 for RHPF and RLPF are different according to equation (5), two separate SRAM arrays (only one SRAM array 350 is shown in FIG. 3) with different number of memory units are necessary for RHPF and RLPF, respectively. For scale n, the input data of RLPF memory is from the reconstructed data at scale n+1, and the input data of RHPF memory is from the DHPF output of decomposition block at scale n+1. For every reconstructed data output, four data samples from RLPF SRAM [in accordance with equation (6)] and six data samples from RHPF SRAM [in accordance with equation (7)] are read out to calculate outputs of RLPF and RHPF respectively. The delays required for reconstructing an ECG signal, as mentioned above, are provided by the SRAM arrays.

Instead of using two separate SRAM arrays to realize the DHPF output delay and the delay inside RHPF respectively, a single SRAM array (such as the SRAM array 350 shown in FIG. 3, but having a sufficiently large number of units 366) may be used. The initial access addresses 360 have to be carefully chosen to realize both the DHPF output delay, and the delay inside RHPF. Thus, the I/O control part of the single SRAM array has comparatively larger circuits and occupies a larger area. However, using a single SRAM array can reduce the number of I/O control part, resulting in reduced hardware area.

Returning to wavelet decomposition, to further reduce the number of I/O control part and hardware area, the SRAM array 320 integrates four single port SRAM 316 units together. For the scales S5 to S8 DLPF implementation, for example, adopting four separate single-port SRAM units 316 using Chartered 0.18 μm technology gives an area of about 160750 μm². However, for the integrated SRAM array 320, the area is only about 105814 μm², which reduces almost 34% hardware area.

The integrated SRAM array 320 works as follows. Different data sequences need to be written into the SRAM array 320, and the sampling rate for each sequence is $f_1$. Memory units are allocated to the different scales S5 to S8 in a sequential manner. Assuming the number of required units for scales n, n+1, n+2 are $P_n$, $P_{n+1}$, $P_{n+2}$, respectively, the memory addresses that allocated to them are 0~($P_n$−1) $P_n$~($P_n$+$P_{n+1}$−1), and ($P_n$+$P_{n+1}$)~($P_n$+$P_{n+1}$+$P_{n+2}$−1) respectively. The addresses for writing and reading are sequential and scale by scale. For DHPF, for example, the memory operation is writing data of scale n, reading data 1 of scale n, reading data 2 of scale n, writing data of scale n+1, reading data 1 of scale n+1, reading data 2 of scale n+1, . . . , in sequence. In FIG. 3, the first multiplexer 322 selects the data 304 that will be written into the SRAM array 320 from different data sequences 330. The control module 326 can generate chip enable (CEN) and write enable (WEN) signals; and memory access address 310.

As multiplication modules are normally complex and occupy large areas, it is an objective of various embodiments to use fewer multiplication modules. According to equations. (3), (4) and (6), it can be observed that the multiplication operation for DLPF, DHPF, and RLPF may be implemented by shifting and adding operations. For RHPF in Eq. (7), multiplication occurs at the higher operation frequency $f_2$. Therefore, only one multiplication module 312 is required for one integrated SRAM array 320 for the different scales S5 to S8. As shown in FIG. 3, the second multiplexer 324 is applied for selecting different multiplication factors. Since non-zero coefficients for different scales are exactly same, the hardware structure can be further simplified.

Thus, the eight scales WT decomposition separates the incoming ECG signal 152 into eight DHPF outputs from scales S1 to S8 and one DLPF output for scale S8. These nine signal sequences represent different characteristics of ECG signal in different bandwidth.

The above decomposition and reconstruction schemes are based on WT, and are suitable for non-downsampling WT. Non-downsampling WT has a "sparse" FIR structure, with a large number of delays and a small number of non-zero coefficients. The SRAM array 320/350 has an operating frequency $f_2$ which, in one embodiment, may only be 32 times higher than the sampling frequency $f_1$. In contrast, using a normal FIR structure which has a large number of both delays and non-zero coefficients, the operating frequency of the FIR structure would need to be at an impractically (around hundreds of times) larger value than the sampling frequency.

When choosing whether to use a single-port SRAM or a double-port SRAM to realise the memory array 320, the number of scales that the memory array 320 processes is a factor. The number of scales that can be processed by an integrated SRAM is, in turn, limited by the following factors.

The first factor is the number of I/O ports that the memory can provide. A single-port SRAM occupies much smaller area as compared with a dual-port one. However, the dual-port memory can perform reading and writing operation at same time, whereas the single-port one can only perform either reading or writing operation during one clock cycle of $f_2$. Therefore, the maximum number of times for reading and writing during one clock cycle of $f_1$ using single-port SRAM is less than that using dual-port memory, resulting in that the maximum permitted number of scales using single-port SRAM is less than that using dual-port SRAM.

The second factor is the ratio between the highest operation clock frequency $f_2$ that the system can support and the sampling rate of the input data sequence $f_1$. The higher the ratio, the more the reading and writing operation can be performed during one clock cycle of $f_1$, resulting in more scales that can be combined together.

The third factor is the number of non-zero coefficients for FIR filters. Assuming there are M non-zero coefficients for the FIR filter of each scale, the maximum number of scales using single-port SRAM and dual-port SRAM can be calculated by equations (8) and (9), respectively.

$$N_s = \left\lfloor \frac{f_2}{f_1 \cdot (M+1)} \right\rfloor \tag{8}$$

$$N_d = \left\lfloor \frac{f_2}{f_1 \cdot M} \right\rfloor \tag{9}$$

where $\lfloor x \rfloor$ is the operation choosing the maximum integer that is not larger than x.

It will be appreciated that shift registers are also usable to realise the decomposition and reconstruction of the ECG signal. However, by using SRAM to facilitate the WT decomposition and reconstruction, area of about 50% can be saved as compared to using conventional shift registers.

Returning to FIG. 1, the electrocardiogram signal reconstruction block 116 processes wavelets belonging to the first to the eighth scales (S1 to S8) and reconstructs an ECG signal from the plurality of wavelets from the first to the eighth scales. Compared to the ECG signal input into the wavelet transformation unit, the reconstructed ECG signal is cleaner in that it has been processed to remove noise. In the embodiment shown in FIG. 1, the electrocardiogram signal reconstruction block 116 includes a first reconstruction block 118 for the fifth to the eighth scales S5 to S8; a second reconstruction block 120 for the first to the fourth scales S1 to S4; and a third reconstruction block 122 for the first to the eighth scales S1 to S8. It will be appreciated that the three reconstruction blocks 118, 120 and 122 may be implementable by memory arrays, such as the memory array architecture shown in FIG. 3, wherein SRAM is used. However, in another embodiment (not shown) the first reconstruction block 118, the second reconstruction block 120 and the third reconstruction block 122 may use shift registers to achieve delay. In a further embodiment (not shown), the first reconstruction block 118, the second reconstruction block 120 and the third reconstruction block 122 may include both shift registers and memory arrays to achieve delay. The first reconstruction block 118 outputs synchronized signals belonging to the high-pass filtered components of the fifth to the eighth scales ($RH_{out}S5$, $RH_{out}S6$, $RH_{out}S7$ and $RH_{out}S8$); the second reconstruction block 120 outputs synchronized signals belonging to the high-pass filtered components of the first to the fourth scales ($RH_{out}S1$, $RH_{out}S2$, $RH_{out}S3$ and $RH_{out}S4$); and the third reconstruction block 122 outputs signals belonging to the low-pass filtered components of the first to the seventh scales ($RL_{out}S1$, $RL_{out}S2$, $RL_{out}S3$, $RL_{out}S4$, $RL_{out}S5$, $RL_{out}S6$ and $RL_{out}S7$). The output of the first to the third reconstruction blocks (118, 120 and 122) may be a reconstructed electrocardiogram signal. The second reconstruction block 120 is coupled to an output of one of the at least one wavelet denoising unit 110 to receive denoised wavelets belonging to the first to the third scales S1 to S3.

B) Data Compression and Decompression

As shown in FIG. 1, the data compression block 106 acts as an interface between both a portion of the output from the wavelet transformation unit 102 and the baseline drift removal unit 108; and the electrocardiogram signal reconstruction block 116. The data compression block 106 receives wavelets of the fifth to the eighth scales S5 to S8, wherein an output of the data compression block 106 is coupled to the input of the first reconstruction block 118.

To minimize the area of storage units, the data compression block 106 utilizes a data compression algorithm, based on the properties of WT decomposition for the WT scales 5~8 DHPF. In various embodiments, the data compression algorithm is computational efficient.

Figure 4:
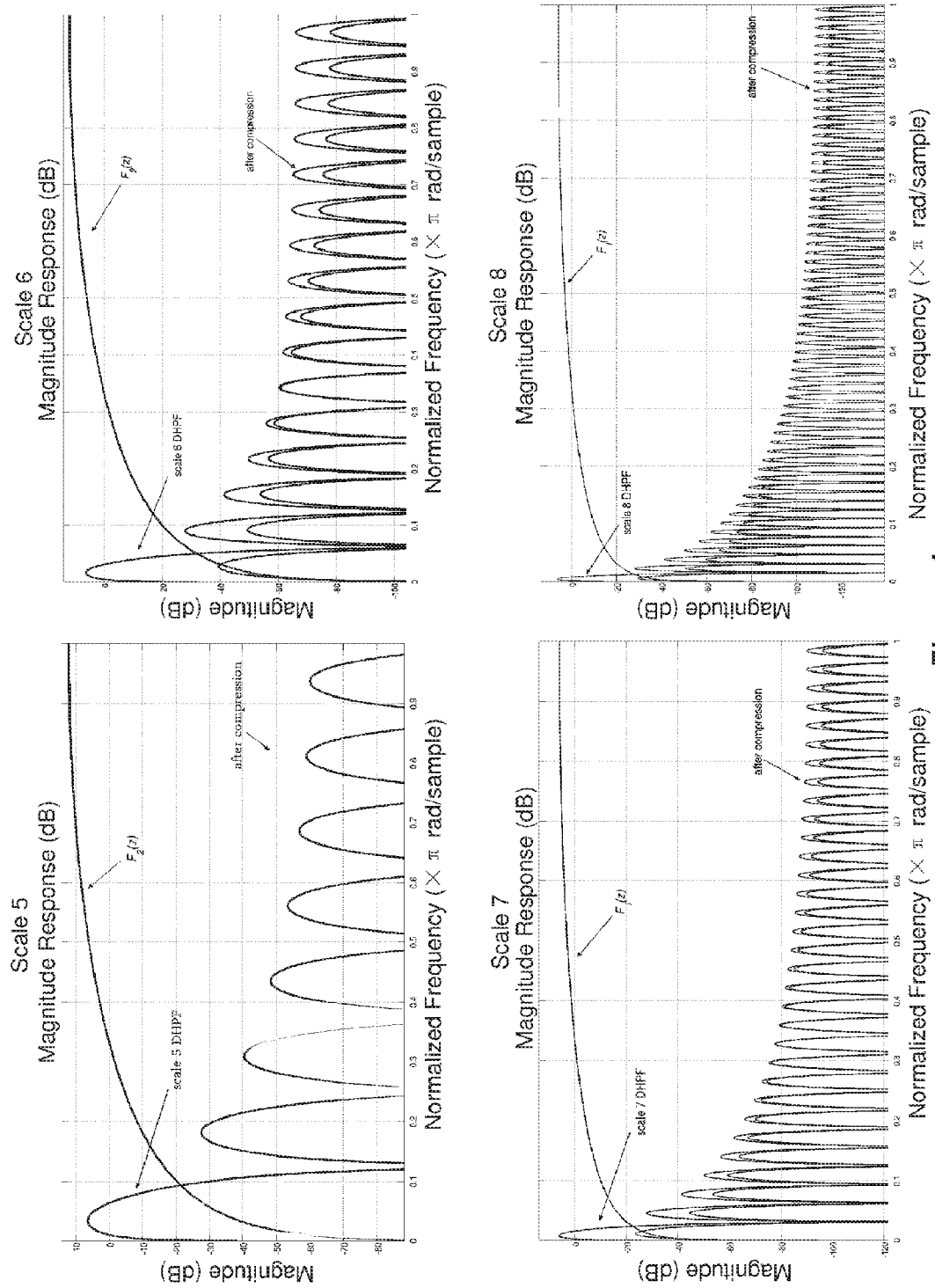
FIG. 4 shows a spectrum of compression filtering.

From FIG. 4, it can be observed that the DHPF outputs of discrete WT for scales S5 to S8 suppress most of the high-frequency components. Therefore, a conclusion may be drawn that the variations between successive samples are much smaller than the values of samples. To minimize the number of required storage units, the variations between samples, instead of the samples themselves, may be stored into memory. Such a data compression scheme can be mathematically expressed by $$c(i)=d(i)-d(i-1) \tag{10}$$

where d(i) and c(i) are the data samples before and after compression, respectively. Equation (10) may also be thought of as a first-order differentiator with the transform function $$F_1(z)=1-z^{-1} \tag{11}$$

Considering DHPF output of scales S5 to S8, it can be observed that the passband of scale S8 is the lowest whereas the passband of scale S5 is the highest. Therefore, comparing different scales, the amplitudes of variations in scale S8 are smallest, whereas the variations in scale S5 are largest. As a result, c(i) in Eq. (10) for scales S5 and S6 may be much larger than that for scales S7 and S8. Therefore, the second-order differentiator instead of first-order differentiator can be adopted for scales S5 and S6 to further reduce the amplitude of variations, as given by $$\begin{aligned}c(i) &= [d(i) - d(i-1)] - [d(i-1) - d(i-2)] \\ &= d(i) - 2d(i-1) + d(i-2)\end{aligned} \tag{12}$$

and its corresponding z domain transform function is $$F_2(z)=1+2z^{-1}+z^{-2} \tag{13}$$

The frequency response of $F_1$ and $F_2$ is shown in FIG. 4. It can be observed that although the proposed differentiator amplifies the components in high-frequency domain slightly, it significantly suppresses the amplitude of components in low-frequency domain. The compressed data is then sequentially written into the SRAM array 320 (see FIG. 3) and thus the requirement of storage units is reduced.

Returning to FIG. 3, in the electrocardiogram signal reconstruction block 116, the stored data needs to be decompressed, and an inverse operation is used. According to equations (11) and (13), the reconstruction filter for scales S7 to S8 is $$G_1(z) = \frac{1}{F_1(z)} = \frac{1}{(1-z^{-1})} \tag{14}$$

and the reconstruction filter for scales S5 to S6 is $$G_2(z) = \frac{1}{F_2(z)} = \frac{1}{(1-2z^{-1}+z^{-2})} \tag{15}$$

From equations (14) and (15), it can be observed that the reconstruction filters are first-order and second-order integrators. They may be infinite impulse filters (IIR) with poles on the unit circle, resulting in instability. However, cascading and $F_i$ and $G_i$, i=1, 2, the poles and zeros compensate each other, and thus the complete system is stable. Thus, the data compression block 106 may be realized using finite-impulse-response filters and the data decompression may be realized using infinite-impulse-response filters, wherein either filter compensates poles and zeros of the other filter.

Figure 5:
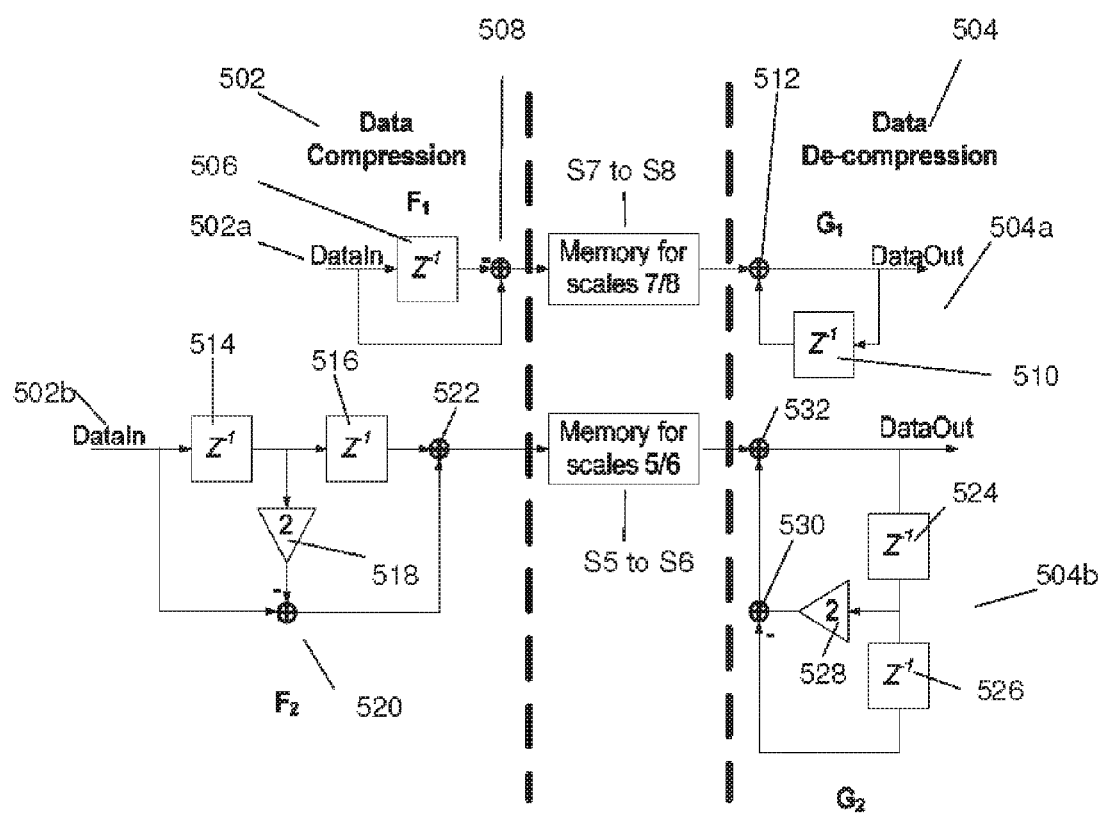
FIG. 5 shows a block diagram of the compression scheme for data compression and decompression.

FIG. 5 shows a block diagram of the compression scheme for the data compression and decompression. The data compression and decompression includes a data compression portion 502 and a data de-compression portion 504. It can be observed that the hardware cost of this scheme is comparatively low. For both the first-order compression 502a and de-compression 504a, each has only one delay unit (506, 510) and one addition unit (508, 512) respectively. For both the second-order compression 502b and de-compression 504b, each has two delay units (514, 516; 524, 526), two addition units (520, 522; 530, 532), as well as one multiplication unit (518; 528). However, the multiplication factor of the multiplication unit is 2, which can be implemented by left shifting the data by 1 bit and padding zero on the least significant bit (LSB). Therefore, in another embodiment, which uses a shift register, there is no need to use a multiplication circuit. Referring to FIG. 3, it will be appreciated that (although not shown) data decompression is performed at the output of the SRAM array 350 before the data enters the multiplication module 312.

II Baseline Drift Removal Unit

As shown in FIG. 1, the baseline drift removal unit 108 acts as an interface between both a portion of the output from the wavelet transformation unit 102 and a portion of the data compression block 106. The baseline drift removal unit 108 is coupled to a respective output of the wavelet transforming unit 102 emitting wavelets belonging to the seventh and the eighth scales S7 and S8. High-pass filters (not shown) with specific cut-off frequency and stop-band attenuation may be used for the baseline drift removal unit 108. However, in such high-pass filters, low-frequency ECG signals with data useful to provide information on a patient's health, may be treated as interference and suppressed as well, resulting in ECG waveform distortion. The cut-off frequency and attenuation may be adjusted to minimize the loss of useful ECG information, but would affect the performance of baseline drift removal. Thus, when using high-pass filters with specific cut-off frequency and stop-band attenuation, a balance has to be struck between baseline drift removal and ECG signal distortion.

Various embodiments, while providing a computational efficient and low cost scheme for hardware implementation, address the problems of using high-pass filters as follows. Similar to the power & area efficient WT decomposition/reconstruction scheme described in the earlier section, various embodiments of the baseline drift removal unit 108 take advantages of the natural properties of WT to remove baseline drift. Various embodiments use an automatic decision scheme to determine whether the WT based scheme has sufficiently removed baseline drift. In circumstances where the WT based scheme can not sufficiently remove baseline drift, additional HPF may be applied. Assuming that a bradycardia of 42 beats per minute is the lowest heart rate to be processed, then the lowest frequency component of the ECG spectrum is 0.7 Hz, and the low cut-off frequency may be as high as the HBR without disturbing the waveform.

Various embodiments use a sampling rate of incoming ECG signal $f_1$ of around 1 kHz to keep high resolution.

Figure 6:
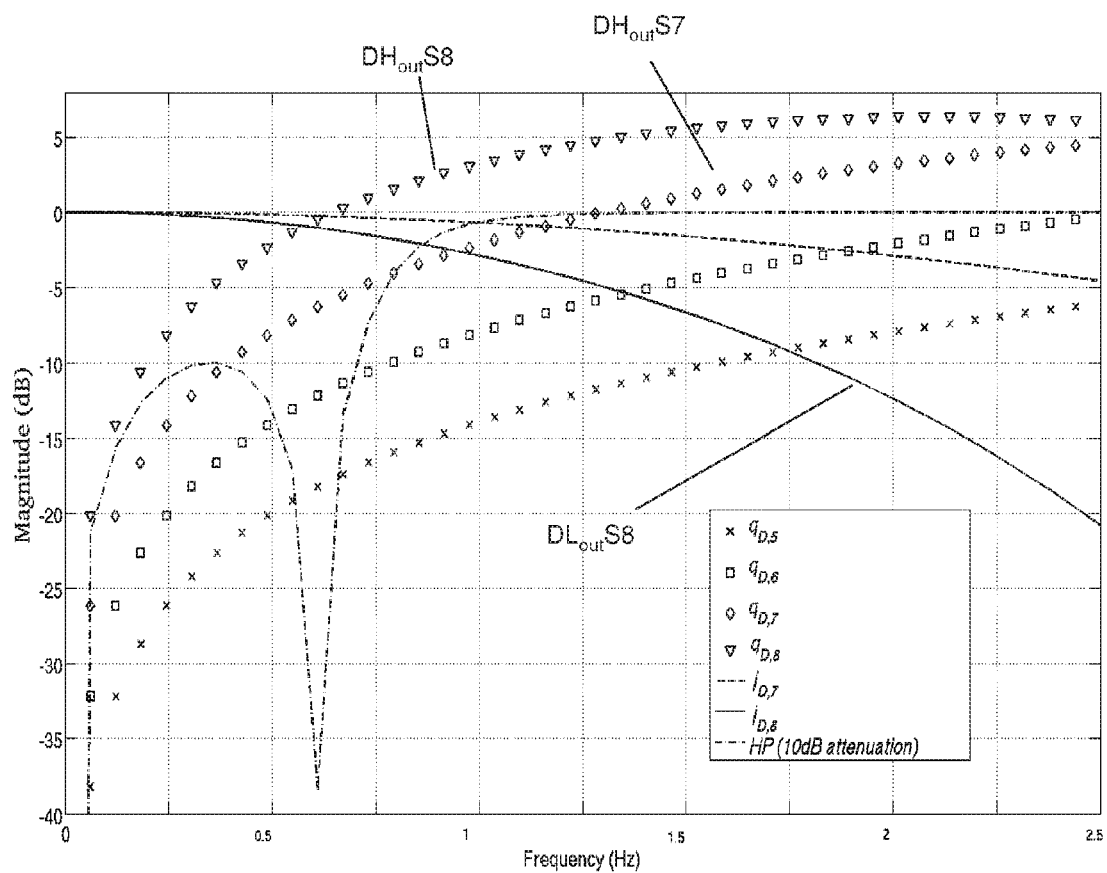
FIG. 6 illustrates the spectrum of WT decomposition filters.

FIG. 6 illustrates the spectrum of WT decomposition filters. As mentioned above, the eight scales WT decomposition (performed by the filter arrangement 164 and the memory array 104 described with respect to FIGS. 2 and 3 respectively) separates the incoming ECG signal into eight DHPF outputs from scales S1 to S8 and one DLPF output for scale S8. From FIG. 6, it is observed that the DC components and the dominant lowest frequency component are resident in the DLPF output of scale S8. At the same time, the DHPF output of each scale also may contain certain low-frequency components. However, attenuation decreases as the scale increases.

It is also observed that almost all the DC components and baseline drifting fall in the DLPF output of scale S8 and DHPF outputs of scale S7 to S8. Various embodiments focus on these three sub-band signals and can be separated into two steps.

In the first step, the DLPF output of scale S8, $DL_{out}S8$, is forced to zero as it is dominated by DC components and lowest frequency components. From FIG. 6, it can be observed that the transition between pass-band and stop-band is quite smooth for both DLPF and DHPF. Therefore, in the first step, the DC components and lowest frequency components are suppressed, while some of the useful ECG information falling into this bandwidth can still remain because the DHPF outputs of scales S7 and S8 are used for reconstruction. The first step may be performed using FIR filtering with linear phase. In the condition that the baseline interference is comparatively small and has low bandwidth, most of the baseline interference can be removed by the first step. The electrocardiogram signal reconstruction block 116 (see FIG. 1) can directly reconstruct clean ECG signals.

On the other hand, if baseline interference is comparatively large, it may be necessary to introduce additional filters to suppress the baseline removal. Two high-pass filters (represented as numeral 166 in FIG. 1) may be applied on the DHPF outputs of scales S7 and S8 (i.e. $DH_{out}S7$ and $DH_{out}S8$ shown in FIG. 1) respectively. Since most of the DC and low-frequency components have already been removed in the first step, the stop-band attenuation requirement of these high-pass filters can be relaxed, resulting in comparatively low computational complexity and hardware cost. Various embodiments may use a chebyshev II IIR filter because of its flat pass-band response and small number of sections. Four such identical IIR filters may be cascaded, in which the cut-off frequency and stop-band attenuation of the IIR filter are 0.7 Hz and 5 dB, respectively. Therefore, totally 20 dB of stop-band attenuation can be achieved.

Figure 7:
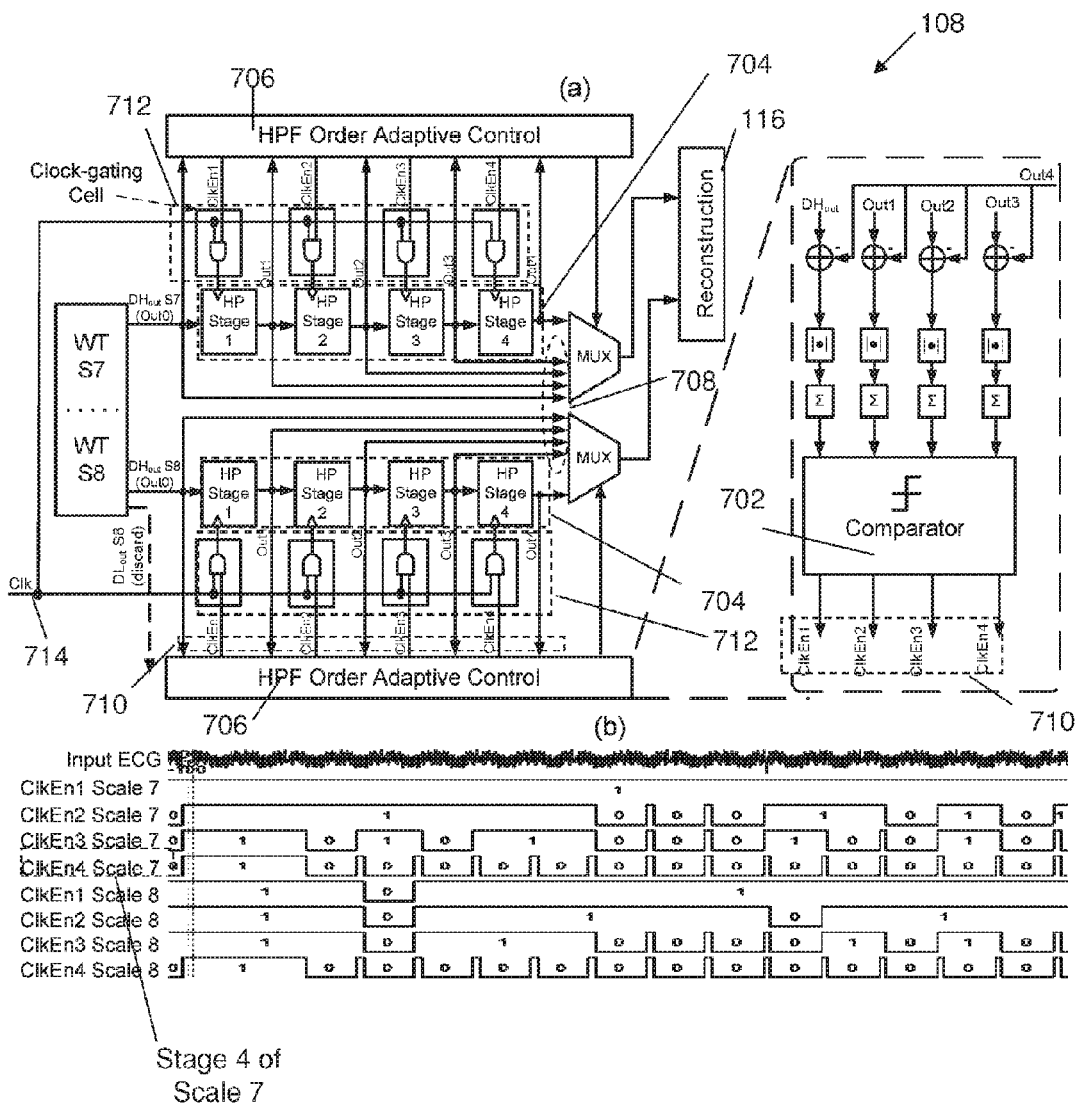
FIG. 7 shows a block diagram of a baseline drift removal unit.

FIG. 7 shows a block diagram of the baseline drift removal unit 108. It is not necessary to switch on all of the four-stage IIR filters of a filter arrangement 704 at the same time. If the baseline drifting is not severe, 20 dB attenuation may not be necessary. Control modules 706, each implementing an adaptive filtering scheme, which can automatically adjust the number of stages that are to be activated to meet the requirement in different conditions, may be used to minimize the operation power.

The number of stages, $P_i$, to meet the requirement value may be calculated by the following formula $$P_i = \frac{1}{L}\sum_{l=1}^{L} |S_{l,i}|^2 \quad i = 0, 1, 2, 3 \tag{16}$$

where L is the number of output samples taken into account, and $S_{l,i}$ is the difference between the lth output of stage i and stage 4. i=0 means that no additional filter operates, and the DHPF outputs of scale 7 and 8 are directly used for clean ECG reconstruction. If the output of stage i has enough capability of baseline removal, the stages larger than i are not necessary and their clock source are latched, resulting in total computational complexity and power consumption reducing.

To minimize the computational complexity, the second order statistic in equation (16) may be replaced by the first order statistic, that is $$A_i = \frac{1}{L}\sum_{l=1}^{L} |S_{l,i}| \quad i = 0, 1, 2, 3 \tag{17}$$

If $A_i$ is smaller than a specified threshold, determined by a comparator circuit 702 of the control module 706, the comparison procedure is finished. The output (indicated as reference numeral 708 in FIG. 7) of stage i is the final output of the filter arrangement 704, and the clock sources of all the stages larger than i can be latched. The adaptive filtering scheme, implemented by the control modules 706, requires that all the filter stages 704 operate periodically for calculating A and comparison. After the number of stages is determined, the clock of the unnecessary filter stages 704 will be latched until the next comparison period comes. For instance, at stage 4 of Scale 7, the clock of all the unnecessary stages are latched, as shown in FIG. 7. Latching of the filters in the filter arrangement 704 occurs as follows. The comparator circuit 702 sends each of a plurality of reset signals 710 to the respective filter of the filter arrangement 704 that is to be activated/de-activated. Each of the reset signals 710 is processed, along with a clock signal 714, by a logic array 712. The output of the logic array 712 then activates/de-activates the respective filter of the filter arrangement 704. In this manner, the control module 706 automatically chooses the minimum number of HPF in the filter stages 704 required in different scenarios, for saving power and minimize the loss of useful ECG components.

Thus, the baseline drift removal block 108 may be realized by an adaptive cascaded filter arrangement 704, the cascaded filter arrangement 704 comprising at least one filter stage. The adaptive cascaded filter arrangement 704 may automatically switch off filter stages unnecessary for performing baseline drift removal. The unnecessary filter stages may be those larger than a filter stage in which the difference in the output value of the filter stage and an output value of the largest filter stage is smaller than a specified threshold. The baseline drift removal unit 108 is connected to scales S7 and S8 (WT S7 and WT S8 of FIG. 7 respectively). In one embodiment, since the attenuation of scale S7 DHPF below 0.7 Hz is larger than that of scale S8 DHPF as shown in FIG. 6, the required filter stages of scale 7 is less than that of scale 8.

III Noise Suppression Block, Adaptive Threshold Based QRS Detection Unit, and HBR Analysis Unit A) Noise Suppression Block As shown in FIG. 1, the noise suppression block 110 acts as an interface between a portion of the output from the wavelet transformation unit 102 and a portion of the input to the electrocardiogram signal reconstruction block 116. Various embodiments use wavelet transform for time-frequency analysis, since an ECG signal is a time-varying biomedical signal. One advantage wavelet transform provides lies in its multiscale information analysis which can used to characterize a signal.

Various embodiments provide a real time QRS detection ASIC based on sum of denoised outputs of DHPF. The QRS detection unit 112 is coupled to the output of the at least one wavelet denoising unit 110 and the output of the wavelet transforming unit 102 emitting wavelets belonging to the fourth scale. To exploit wavelet inter-scale dependencies, various embodiments multiply adjacent outputs of DHPF to enhance edge structures while weakening noise. Thereafter, a threshold may be calculated and imposed on the products, instead of on the outputs of DHPF, to identify the important features.

Figure 8:
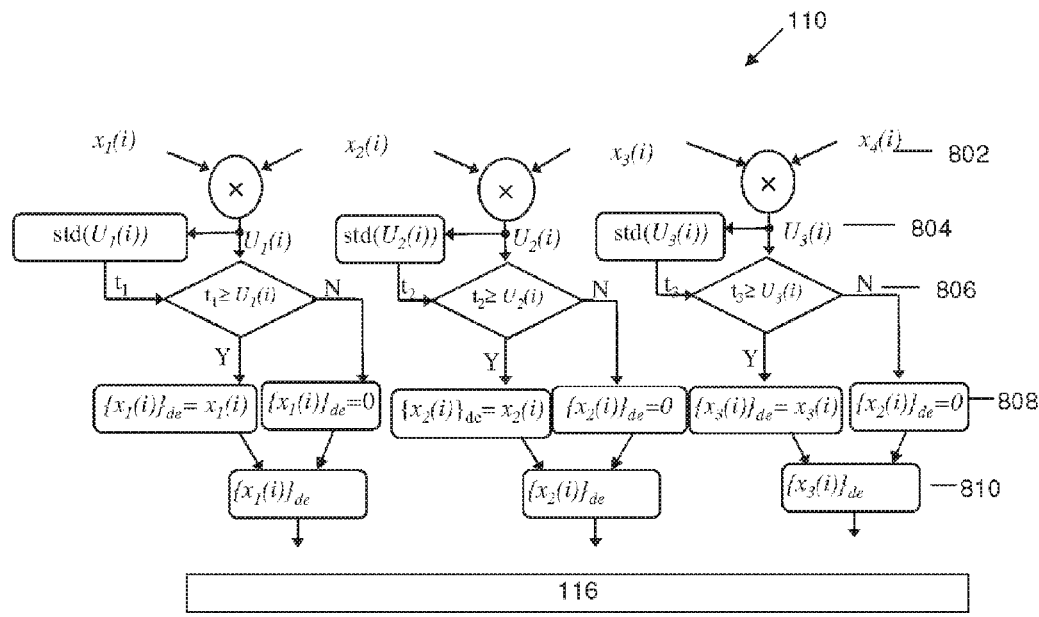
FIG. 8 shows the algorithm implemented by a noise suppression block.

To enhance QRS detection, signal preprocessing to reduce noise reduction is preferred. FIG. 8 shows the algorithm implemented by the noise suppression block 110. Briefly, the algorithm assumes that noise yields small-value wavelet outputs while large-value outputs contain mostly of the actual ECG components. By taking advantage of dependency information between wavelet scales, two adjacent subbands are multiplied to amplify significant features and dilute noise. Thereafter, an adaptive threshold is calculated and imposed on the products, instead of the wavelet coefficients, to merge the merits of the threshold-based algorithm and wavelet inter-scale dependencies. A significant output of DHPF coefficient $\{x_n(i)\}_{de}$ is identified if its corresponding multiscale products value $U_n(i)$ is greater than a threshold $t_n$.

The algorithm shown in FIG. 8 has the following features:
1. In 802, the outputs of DHPF of digital input ECG signal up to scale levels 4 (n=1, 2, 3, 4) are computed.
2. In 804, the multiscale product $U_n(i)$ is computed as $$U_n(i) = x_n(i) \cdot x_{n+1}(i) \quad (18)$$

3. In 806, the thresholds $t_n$ are preset by calculating the standard deviation of $U_n(i)$ for every window with a specified number of samples, $$t_n = \text{std}\{U_n(i)\}, n=1,2,3 \quad (19)$$

where std{•} is the operation of calculating the standard deviation, and the number of samples is 1024.

4. In 808, the outputs of DHPF $x_n(i)$ are denoised based on the threshold $t_n$ $$\{x_n(i)\}_{de} = \begin{cases} x_n(i), & U_n(i) \geq t_n \\ 0, & U_n(i) < t_n \end{cases}, n = 1, 2, 3 \quad (20)$$

5. In 810, the noise-suppressed $\{x_n(i)\}_{de}$ are fed into the electrocardiogram signal reconstruction block 116 for clean ECG reconstruction.

B) Adaptive Threshold Based QRS Detection Unit

Figure 9:
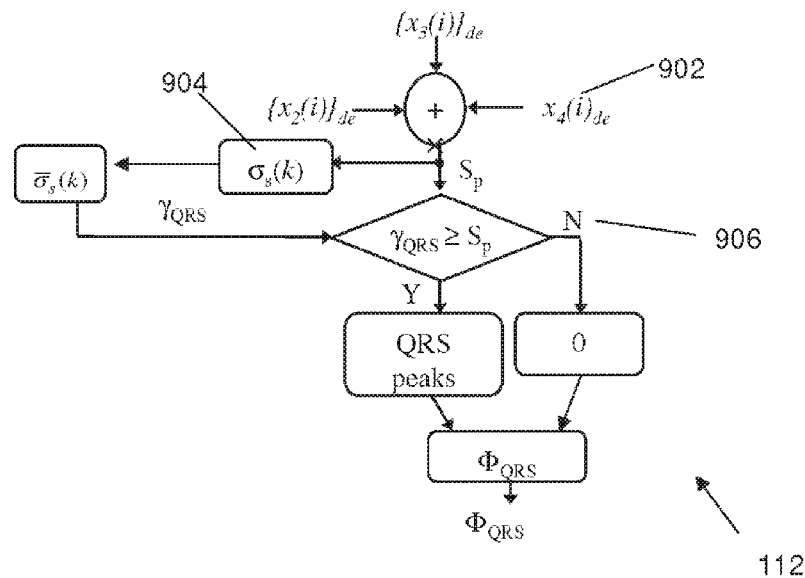
FIG. 9 shows the algorithm implemented by a QRS detection unit.

As shown in FIG. 1, the QRS detection unit 112 receives input from the noise suppression block 110. FIG. 9 shows the algorithm implemented by the QRS detection unit 112.

In 902, for QRS detection, the denoised signals $\{x_n(i)\}_{de}$ are fed into a summation system, where the denoised outputs of DHPF are summed point-by-point to emphasize the QRS complex while suppressing the noise. The summation $S_p(i)$ can be defined as $$S_p(i) = \{x_2(i)\}_{de} + \{x_3(i)\}_{de} + x_4(i) \quad (21)$$

In 904, to make the decision for detecting QRS peaks, an adaptive threshold-based scheme is applied to the feature waveform generated from the summation stage. The thresholding scheme can be formulated as:

$$\Phi_{QRS}(i) = \begin{cases} 1, & S_p(i) \geq \gamma_{QRS} \\ 0, & S_p(i) < \gamma_{QRS} \end{cases} \quad (22)$$

where $\Phi_{QRS}$ indicates the position of QRS peaks and $\gamma_{QRS}$ denotes the adaptive threshold. The adaptive threshold $\gamma_{QRS}$ can be calculated as follows. The instant standard deviation of $S_p(i)$ is calculated for every window with a specified number of samples, and is denoted by $\sigma_s(k)$, where k denotes the kth window. The number of samples per window may be 1024. The standard deviation $\overline{\sigma}_s(k)$ is updated in every window according to the instant standard deviation $\sigma_s(k)$ $$\overline{\sigma}_s(k) = \lambda \cdot \overline{\sigma}_s(k) + (1-\lambda) \cdot \sigma_s(k) \quad (23)$$

where $\lambda$ is referred to as the "forgetting factor" with $0 \leq \lambda \leq 1$. Finally, the adaptive threshold may be given by $$\gamma_{QRS} = c \cdot \overline{\sigma}_s(k) \quad (24)$$

where c is an adjustable constant. According to equations (23) and (24), it can be seen that each new value of the threshold is determined from the prior and current values of the threshold itself. In 906, A QRS peak is detected if the featured signal (i.e., $S_p(i)$) exceeds the threshold. The value of the threshold is then updated each time when a new window of ECG signal comes. Thus from 902 to 906, a wavelet summation unit of the QRS detection unit 112 sums denoised wavelets $\{x_n(i)\}_{de}$ from the at least one wavelet denoising unit 110 (see FIG. 1) and the wavelets from the wavelet transforming unit 102, wherein QRS peaks are detected when the summed wavelets exceed an adaptive threshold value.

C) Heart Beat Rate Prediction & Classification

As shown in FIG. 1, the HBR analysis unit 114 receives input from QRS detection unit 112.

The QRS peak is detected by the real-time adaptive QRS peak detection algorithm used by the QRS detection unit 112. The QRS peak directly reflects the heart beat rate (HBR) and thus its change is a good indicator for classifying potential heart diseases. For example, normally HBR larger than 90 bpm or less than 60 bpm may indicate tachycardia or bradycardia, respectively. However, some patients naturally have somewhat faster or slower HBR in normal status, and thus simply setting a hard decision threshold would not be accurate. Various embodiments use a more accurate classification for the individual status of different patients.

Figure 10A:
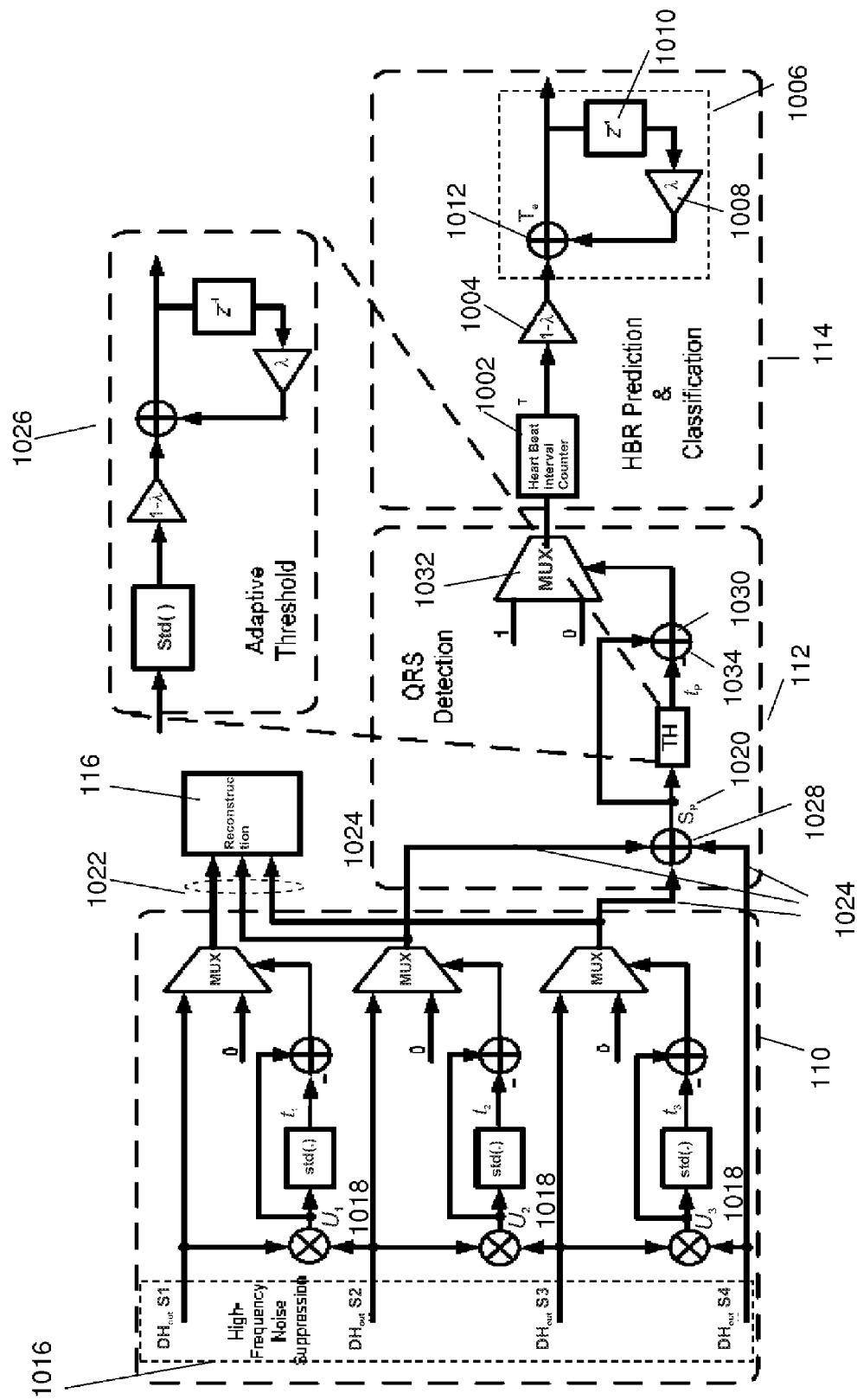
FIG. 10A shows a block diagram of a prediction scheme used by a HBR analysis unit.

FIG. 10A shows a block diagram of a prediction scheme used by the HBR analysis unit 114. The HBR analysis unit 114 uses an adaptive prediction scheme which uses a forward prediction algorithm to track the change of HBR and to further predict symptoms of patients.

The HBR analysis unit 114 includes a heart beat interval counter 1002 coupled to two multiplication modules: a first multiplication module 1004 and a second multiplication module 1008. The first multiplication module 1004 is coupled to a feedback arrangement 1006. The feedback arrangement 1006 includes the second multiplication module 1008, a delay unit 1010 and a summation unit 1012. The HBR analysis unit 114 may be realized by a Field Programmable Gate Array (FPGA), Application Specific Integrated Circuits (ASIC) or be implemented by software.

The HBR analysis unit 114 predicts QRS peak intervals based on a forward prediction algorithm. The forward prediction algorithm may be based on summing previous QRS peak intervals weighted with a forgetting factor, the forgetting factor determining the number of previous QRS peak intervals included for HBR analysis. Further detail on the forward prediction algorithm is as follows.

Assuming the nth detected QRS peak interval is T(n), then the updated prediction of QRS peak interval (i.e. the output of the feedback arrangement 1006) can be obtained as $$Te(n) = \sum_{k=1}^{M} w_k T(n-k) \tag{25}$$

where M is the order of taps and $w_k$ is the tap weights. The prediction algorithm of equation (25) may be implemented by a M-tap FIR filter, as shown in FIG. 2, whereby M taps of shift delay and multiplication are required. To reduce hardware cost, the above algorithm may be approximated and simplified. Various embodiments implement a recursive scheme (realised by the feedback arrangement 1006 and the first multiplication module 1004) given by $$Te(n) = \lambda Te(n-1) + (1-\lambda)T(n-1) \tag{26}$$

where $\lambda$ is the forgetting factor, which is less than but close to 1. Expanding equation (26), the following is obtained $$Te(n) = \lambda[\lambda Te(n-2) + (1-\lambda)T(n-2)] + (1-\lambda)T(n-1) = \ldots \tag{27}$$
$$= \lambda^n Te(0) + \lambda^{n-1}(1-\lambda)T(0) + \lambda^{n-2}(1-\lambda)T(1) + \ldots +$$
$$\lambda(1-\lambda)T(n-2) + (1-\lambda)T(n-1)$$

Assuming Te(0)=0, and defining the tap weights $w_n = \lambda^{n-1}(1-\lambda)$, $w_{n-1} = \lambda^{n-2}(1-\lambda)$, ... $w_1 = (1-\lambda)$, equation (27) can be represented by $$Te(n) = \sum_{k=1}^{n} w_i T(n-k) \tag{28}$$

which is exactly the forward prediction in Eq. (25) by setting M=n.

In various embodiments, the value $\lambda$ dominates the sensitivity of the proposed prediction algorithm, which is a measure of the memory of the previous input data. The larger the forgetting factor $\lambda$, the longer the memory of the previous input, resulting in a long-term prediction with slower prediction change. Even when HBR of the patient varies rapidly within a certain time duration, the long-term prediction can still be able to obtain the stable average HBR without large perturbation. The long-term prediction can indicate the average HBR of the patient in a comparatively long observation window, and can reflect the long-term change trend of the average HBR with less effect by instant HBR variation. Therefore, doctors can use this long-term observation as a baseline reference for a patient in a normal status. On the other hand, the smaller the forgetting factor $\lambda$, the shorter the memory of the previous input, resulting in a short-term prediction with rapid prediction change. This short-term prediction can be used to track the most recent or rapid change of HBR, indicating whether the patient is undergoing abnormal cardiac status. The long-term and short term prediction can work together. If the two observations are overlapped, the short-term observation will vary around the long-term observation. The long-term observation may be treated as the baseline, indicating the trend of HBR drift under normal status. The upper and lower thresholds may be specified according to this baseline, respectively. If the short-term observation exceeds the specific upper threshold, a tachycardia can be discriminated. If the short-term observation exceeds the specific lower threshold, on the other hand, a bradycardia can be discriminated. Such a classification scheme is more accurate than that using hard decision threshold, because the baseline of individual status for different patients is taken into consideration. In various embodiments, the recursive forward prediction algorithm implemented by the feedback arrangement 1006 and the first multiplication module 1004 may be used to track the trend of HBR change long-term and short-term prediction by setting $\lambda$=0.998 and 0.875 respectively. The long-term prediction serves as a baseline reference indicating the long-term change trend of the average HBR. The short-term prediction tracks the rapid change of HBR and filters occasional changes caused by strong emotions or exercise. Setting an appropriate threshold based on long-term prediction and observing the short-term prediction, more accurate arrhythmias classification for the individual status of different patients can be achieved.

FIG. 10A also shows the HBR analysis unit 114 coupled to an output of the QRS detection unit 112. The QRS detection unit 112 is coupled to the noise suppression block 110.

The DHPF outputs 1016 for adjacent scales (from scales S1 to S4) are multiplied to obtain $U_n$ 1018 to amplify significant features and dilute noise. The threshold of denoising $t_n$ is calculated from the standard deviation of $U_n$ 1018. The noise-suppressed DHPF outputs 1022 are fed into the electrocardiogram signal reconstruction block 116 for clean ECG reconstruction. The QRS detection unit 112 calculates the summation $S_p$ 1020 of the de-noised DHPF outputs 1024 from scales S2 to S3 and DHPF output $DH_{out}$ S4 to emphasize the QRS complex while suppressing noise. An adaptive recursive tracking algorithm is applied to update the threshold $t_p$ of the adaptive threshold circuit 1026, which is calculated from the standard deviation of $S_p$ 1020. The QRS detection unit 112 may be realized using any of a Field Programmable Gate Array (FPGA), Application Specific Integrated Circuits (ASIC) or be implemented by software. In FIG. 10A, the QRS detection unit 112 includes a wavelet summation unit 1028, an adder 1030; and the QRS peaks may be detected using a subtractor circuit (represented as a "−" sign indicated by the reference numeral 1034) and multiplexer 1032. As mentioned above, the adaptive threshold value $t_p$ may be derived from a standard deviation of a number of sampled summed wavelets.

FIG. 10B shows a die photo of the electrocardiogram signal processing system 100 of FIG. 1, fabricated using 0.18 μm CMOS technology, along with several of the chip specifications. The memory of the die may share the same clock source with the ΣΔ ADC in the acquisition front-end, which may use 32 kHz for oversampling, and a 1 kHz clock generated by a frequency divider. The die size is 1.2×2.5 mm² including 48 k standard cell instances and 4 SRAMs with totally 140 kbits memory units. Benefited from the intrinsic integrated algorithm and the corresponding dedicated WT structure, the total power consumption of whole chip is only 29 μW with 1V power supply (25° C.).

IV Electrocardiogram Signal Processing System Using Dyadic Wavelet Transform Multiscale-Product Based QRS Complex Detection Algorithm (DYWT-MP-QRS)

Figure 11:
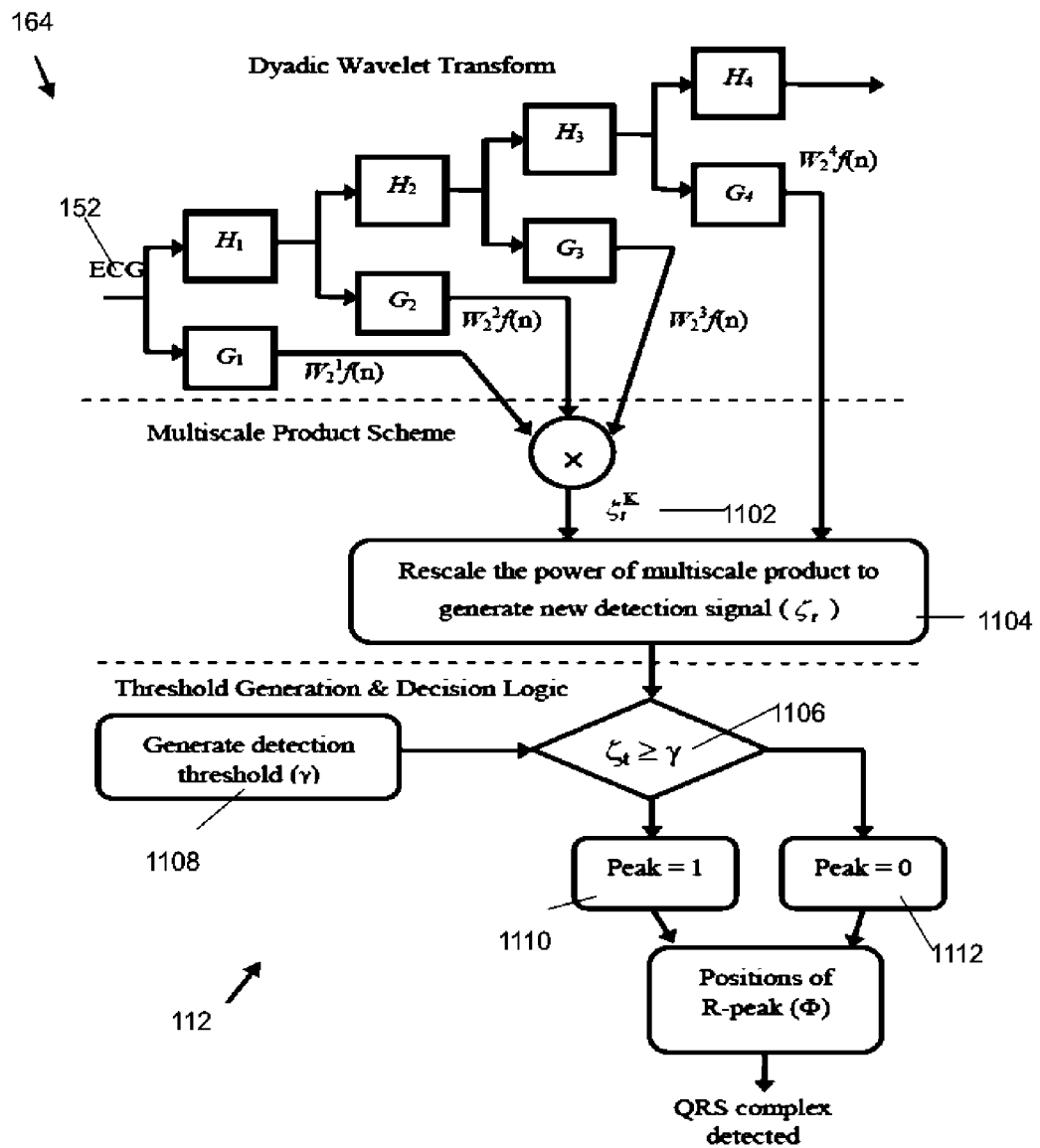
FIG. 11 shows, according to an embodiment, the architecture of a filter arrangement and noise suppression block, along with the algorithm implemented by a QRS detection unit, of an electrocardiogram signal processing system.

FIG. 11 shows, according to an embodiment, the architecture of the filter arrangement 164, along with the algorithm implemented by the QRS detection unit 112, of the electrocardiogram signal processing system 100 of FIG. 1.

The QRS detection algorithm used by the QRS detection unit 112 is based on wavelet multiscale product and a simple decision algorithm. Since wavelet multiscale product and rescaled power of the wavelet multiscale product are considered to achieve good detection accuracy, a decision algorithm based on an amplitude comparison to a simple threshold may be employed, where no search-back is used. One detection threshold needs only to be calculated, compared to known systems which use four thresholds at scales 1 to 4 to obtain the location set of "modulus maxima" across the scales.

As shown in FIG. 11, for discrete-time signals, the Dyadic Wavelet Transform (DYWT) of a discrete signal (i.e. the ECG signal 152) $S_2^{j-1}f$ (j=1) is computed as in S. Mallat, and S. Zhong, "Characterization of signals from multiscale edges," *IEEE* Trans. Pattern Analysis and Machine Intelligence, vol. 14, pp. 710-732, 1992. At each scale level $2j$, DYWT decomposes $S_2^{j-1}f(n)$ into $W_2^j f(n)$ and $S_2^j f(n)$.

$$W_{2^j}f(n) = \frac{1}{\lambda_i} \cdot S_{2^{j-1}}f(n) * G_j; \ j = 1, 2, 3, 4 \quad (29)$$

$$S_{2^j}f(n) = S_{2^{j-1}}f(n) * H_j; \ j = 1, 2, 3, 4 \quad (30)$$

where * is the convolution operator and low-pass subband $S_2^j f(n)$ and $W_2^j f(n)$ are implemented with FIR filters as follows:

$$W_{2^j}f(n) = \frac{1}{\lambda_i} \cdot \sum_{i \in Z} g_i S_{2^{j-1}}f(n - 2^{j-1}i), \quad (31)$$

$$S_{2^j}f(n) = \sum_{i \in Z} h_i S_{2^{j-1}}f(n - 2^{j-1}i) \quad (32)$$

where $h_i$ and $g_i$ are low-pass and high-pass coefficients, respectively and are deployed from S. Mallat, and S. Zhong, "Characterization of signals from multiscale edges," *IEEE* Trans. Pattern Analysis and Machine Intelligence, vol. 14, pp. 710-732, 1992. The wavelet used for DYWT in various embodiments is chosen as the first order derivatives of a smooth function (a cubic spline function, see S. Mallat, and S. Zhong, "Characterization of signals from multiscale edges," *IEEE* Trans. Pattern Analysis and Machine Intelligence, vol. 14, pp. 710-732, 1992), the DYWT $W_2^j f(n)$ can be interpreted as the derivatives of local smooth (average) of $f_t$ at scale j (S. Mallat and W. L. Hwang, "Singularity detection and processing with wavelets," *IEEE* Trans. Inform. Theory, vol. 38, pp. 617-643, February 1992). Hence, if $f_t$ has some singular points, $W_2^j f(n)$ will appear as modulus maxima at these locations. The amplitude of noise modulus maxima will decrease from small scale to large scales while the amplitude of signal modulus maxima will increase from small scales to large scales in the wavelet domain (S. Mallat, and S. Zhong, "Characterization of signals from multiscale edges," *IEEE* Trans. Pattern Analysis and Machine Intelligence, vol. 14, pp. 710-732, 1992), (S. Mallat and W. L. Hwang, "Singularity detection and processing with wavelets," *IEEE* Trans. Inform. Theory, vol. 38, pp. 617-643, February 1992). Therefore, multiscale-product sequence $\xi_t^K$ (indicated as reference numeral 1102 in FIG. 11) sharpens and enhances the modulus maxima dominated by scale edges and at the same time suppresses the modulus maxima dominated by noises. Considering multiscale product of the first κ scale sequences in wavelet domain at time index t:

$$\xi_t^K = \prod_{j=1}^{K} W_{2^j}f; \ j = 1, 2, 3 \quad (33)$$

The power of $\xi_t^K$ is rescaled in step 1104 to that of $W_2^j f(n)$ by $\chi$ and $\psi$ to get a new normalized detection signal $\zeta_t$ and it can be defined as in equation (34)

$$\zeta_t = \sqrt{\frac{\chi}{\psi}} \cdot \xi_t^K \quad (34)$$

where $$\chi = \sum_{n=1}^{N} (W_{2^4}f(n)) \cdot (W_{2^4}f(n)); \ \text{and} \ \psi = \sum_{n=1}^{N} \xi_t^K(n) \cdot \xi_t^K(n).$$

Since the wavelet coefficients corresponding to the signal are enhanced in the new detection signal $\zeta_t$, the local maxima (minima) in $\zeta_t$ can be accurately identified by applying a simple scheme of thresholding for the decision making stage.

To perform the decision making for detecting QRS complexes, in 1108 an interval-dependent threshold scheme is applied to the new detection signal. Assume a detection threshold is γ and is calculated in each interval between two consecutive QRS intervals and updated once for every interval. To determine γ, the standard deviation of $\zeta_t$ is computed in equation (35):

$$\sigma_w(j) = \sqrt{\frac{1}{N}\sum_{i=1}^{N}(x_i - \overline{x}_i)^2}, \; x_i = (\zeta_t)_i \quad (35)$$

where N is the number of samples. The standard deviation $\sigma_w(j)$ is updated every N=1024 samples and the mean value of $\zeta_t$ is almost zero per every 1024 samples. Therefore, equation (35) can be simplified as:

$$\sigma_w(j) = \sqrt{\frac{1}{N}\sum_{i=1}^{N}(x_i)^2}, \; x_i = (\zeta_t)_i \quad (36)$$

and setting the detection threshold as $$\gamma = c \cdot [\sigma_w(j)] \quad (37)$$

where constant c is used to adjust the threshold γ imposed on $\zeta_t$. From comparison in 1106, the threshold scheme can then be formulated in 1110 and 1112 respectively as $$\Phi = \begin{cases} 1 & \zeta_t \geq \gamma \\ 0 & \zeta_t < \gamma \end{cases} \quad (38)$$

Φ is the vector that contains the site of R peak points. The constant c is adjustable to achieve good detection accuracy.

Power is proportional to $\alpha \cdot C_L \cdot V_{DD}^2 \cdot f$, where α is the switching activity, f is the frequency, $C_L$ is the load capacitance, and $V_{DD}$ is the supply voltage. Consequently, low-power digital design focuses on reducing α, $C_L$, $V_{DD}$, and f. These parameters can be reduced through algorithmic, architectural and circuit techniques.

Figure 12:
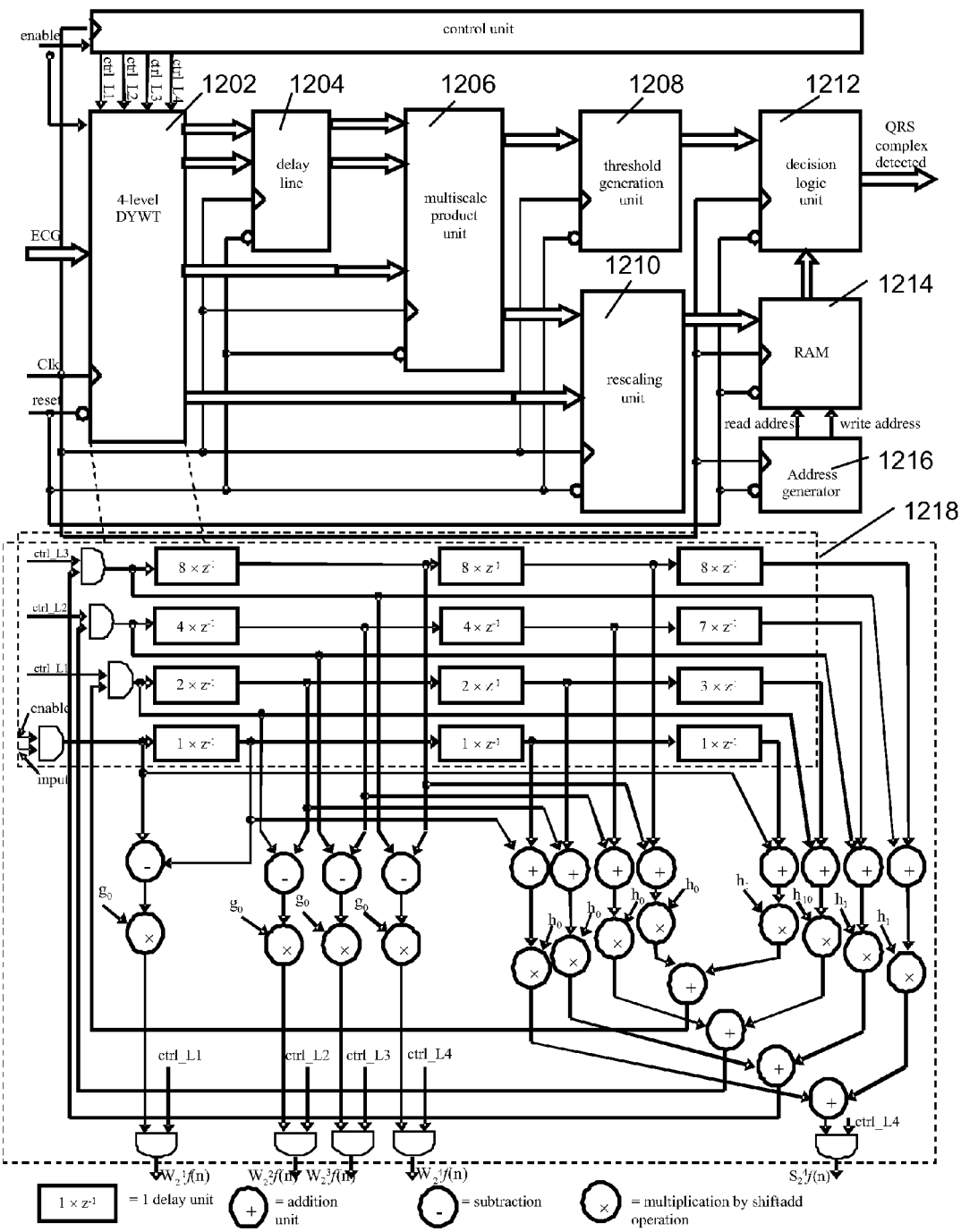
FIG. 12 shows architecture implementing an algorithm used by various embodiments of an electrocardiogram signal processing system

Various embodiments reduce design complexity related to the effective capacitance (i.e. $\alpha \cdot C_L$). FIG. 12 shows architecture implementing an algorithm used by various embodiments of an electrocardiogram signal processing system 1200.

The electrocardiogram signal processing system 1200 includes a wavelet transformation unit 1202, a delay block 1204, a multiscale product block 1206, a threshold generation block 1208, a rescaling block 1210, a decision logic unit 1212, a RAM block 1214 and an address generator block 1216.

In the embodiment shown in FIG. 12, the wavelet transformation unit 1202 uses DYWT as described with reference to FIG. 11. As shown in FIG. 11, the DYWT may be implemented with FIR filters $H_1, H_2, H_3, H_4, G_1, G_2, G_3, G_4$ and the transfer functions of the low-pass and high-pass filters at scale level j=1 can be expressed as $$H_1(z) = h_0 + h_1 z^{-1} + h_2 z^{-2} + h_3 z^{-3} \quad (39)$$

$$G_1(z) = g_0 + g_1 z^{-1} \quad (40)$$

Since the coefficients are symmetric (i.e., $h_0 = h_3$, $h_1 = h_2$ and $g_0 = -g_1$) (as per Y. Xu et. al., "Wavelet transform domain filters: A spatially selective noise filtration technique," *IEEE Trans. Medical Imaging*, vol. 22, pp. 323-331, 2003), the number of multipliers may be reduced into half. The transfer functions become:

$$H_1(z) = h_0(1+z^{-1}) + h_1(z^{-1}+z^{-2}) \quad (41)$$

$$G_1(z) = g_0(1-z^{-1}) \quad (42)$$

Since the data input to low-pass and high-pass filters are the same at each scale level, the number of delay elements can therefore be shared to minimize the hardware cost. The order increases with scale level increases because $(2^j-1)$ zeros coefficients are inserted between two non-zero coefficients. However the numbers of non-zero coefficients remain the same at each level, the required number of multiplications and addition are the same at each level and delay elements are increased by 2 times. With this architecture, DYWT scale level 1 to 4 (labeled as numeral 1218 in FIG. 12) requires 12 multiplications, 12 additions, 4 subtraction and 47 delay elements.

The delay block 1204 may have 11 D flip-flops (i.e., 11 clock cycles) to align three high-pass outputs (i.e. the outputs from the filters G1, G2, G3 of FIG. 11) to produce the multiscale product signal $\xi_t^K$ (indicated as reference numeral 1102 in FIG. 11). The product signal $\xi_t^K$ is first squared and then the squared products summed for every 1024 samples to obtain the scaling factor ψ of the rescaling block 1210, which is updated for each of the 1024 samples. The same process may be applied to calculate the scaling factor χ of the rescaling block 1210. The scaling factor χ is divided by the scaling factor ψ, the result square root and multipled with $\xi_t^K$ to get the final detection signal $\zeta_t$. The final detected signal is stored into the RAM block 1214 for a few cycles until the threshold value $\zeta_t$ is generated. Techniques may be employed to reduce the memory size and write address is therefore one clock cycle delayed by the read address.

The threshold generation block 1208 calculates the dynamic threshold γ as in equation (37) by multiplying the standard deviation of $\zeta_t$ and constant c. The procedure of generating the QRS detection threshold γ may be as follows. The 8 bit $\zeta_t$ is squared and accumulated 1024 times, and the summation is stored in a register. The QRS detection threshold γ is generated by dividing the summation by 1024 (right-shift 10 bits), square-rooting to get the dynamic deviation $\sigma_w(j)$, then multiplying $\sigma_w(j)$ with constant c to get final γ. By monitoring the difference of γ and $\zeta_t$, the R-peak can be detected.

Figure 13:
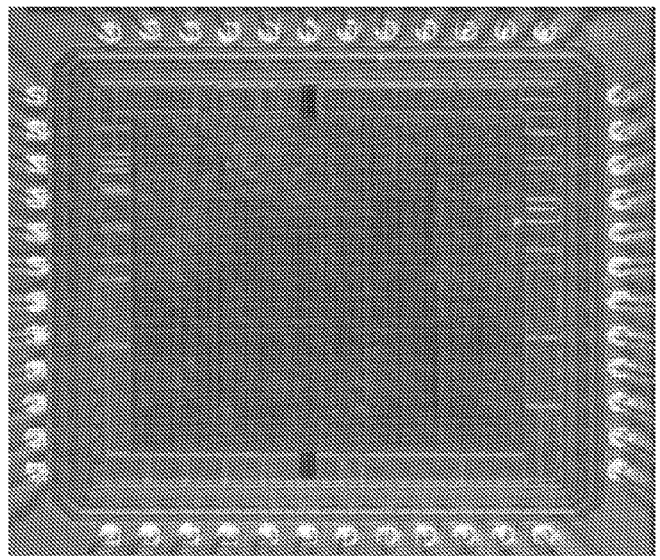
FIG. 13 shows a die photo of a fabricated electrocardiogram signal processing system according to an embodiment.

FIG. 13 shows a die photo of the electrocardiogram signal processing system 1200 fabricated using Chartered 0.18 μm CMOS technology.

Figure 14:
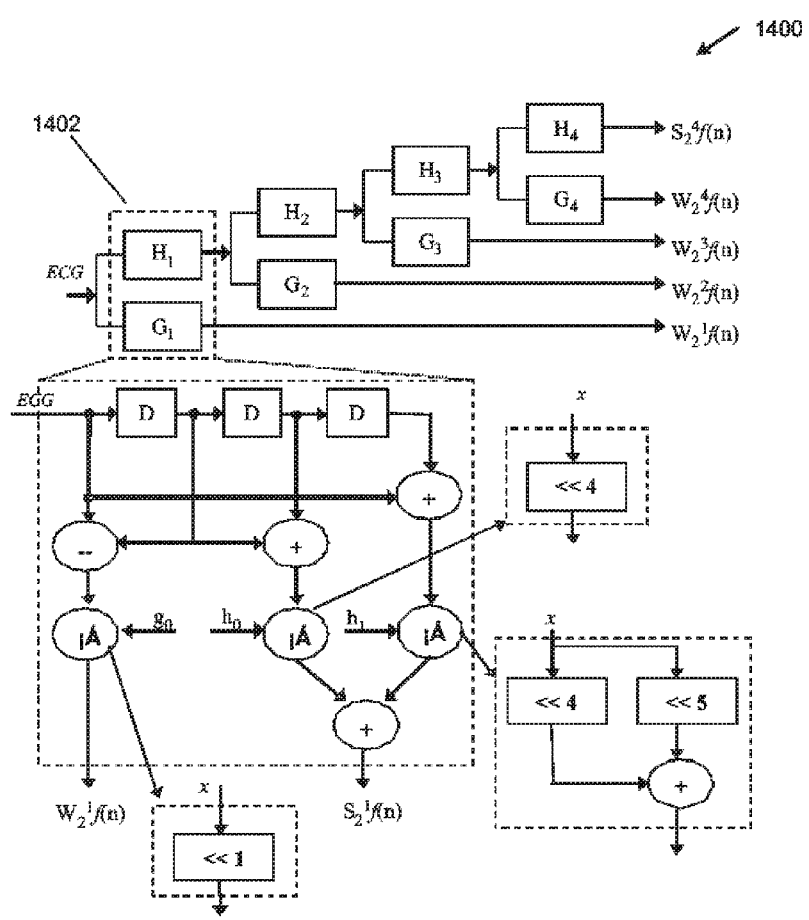
FIG. 14 shows dyadic wavelet transformation architecture usable by an electrocardiogram signal processing system according to various embodiments.

FIG. 14 shows dyadic wavelet transformation architecture 1400 usable by an electrocardiogram signal processing system according to various embodiments.

The architecture 1400 uses a QRS detection algorithm based on wavelet multiscale product and a simple decision algorithm. Since the wavelet multiscale product and rescaled power of the product are considered to achieve good detection accuracy, a decision algorithm based on an amplitude comparison to a simple thresholding method can be employed, wherein no search back is used. With this architecture, only one detection threshold needs to be calculated, while other known systems may use four thresholds at scales 21 to 24 to obtain the location set of "modulus maxima" across the scales. The algorithm may be summarized as follows:

$$W_{2^{j+1}}f(n) = \frac{1}{\lambda_j} \cdot S_{2^j}f(n) * G_j; \; j = 0, 1, 2, 3 \quad (43)$$

$$S_{2^{j+1}}f(n) = S_{2^j}f(n) * H_i; \; j = 0, 1, 2, 3 \quad (44)$$

where * is the convolution operator and low-pass subband $S_2^j f(n)$ and a high-pass subband $W_2^j f(n)$. The $S_2^j f(n)$ and $W_2^j f(n)$ are implemented with linear phase FIR filters since their coefficients are symmetric in nature. The wavelet used for DYWT may be first-order derivatives of a smooth function (a cubic spline function, such as the one in [S. Mallat, and S. Zhong, "Characterization of signals from multiscale edges," *IEEE* Trans. Pattern Analysis and Machine Intelligence, vol. 14, pp. 710-732, 1992]), whereby $W_2^j f(n)$ may appear as modulus maxima at these locations if $S_2^0 f(n)$ (i.e., an ECG signal 1402 in this case) has some singular points. The amplitude of noise modulus maxima may decrease from small scale to large scales in the wavelet domain (S. Mallat, and S. Zhong, "Characterization of signals from multiscale edges," *IEEE* Trans. Pattern Analysis and Machine Intelligence, vol. 14, pp. 710-732, 1992). Therefore, multiscale-product $\xi_t^K$ sharpens and enhances the modulus maxima dominated by scale edges and at the same time suppresses the modulus maxima dominated by noise. The multiscale product of the first κ scales in wavelet domain at time index t $$\xi_t^K = \prod_{j=1}^{K} W_{2^j} f(n); \, j = 1, 2, 3 \tag{45}$$

The power of $\xi_t^K$ is rescaled to that of by $\chi$ and $\gamma$ to obtain a new normalized detection signal $\zeta_t$ defined as:

$$\zeta_t = \sqrt{\frac{\chi}{\psi}} \cdot \xi_t^K \tag{46}$$

where $$\chi = \sum_{n=1}^{N} W_{2^j} f(n) \cdot W_{2^j} f(n), (j=4) \text{ and } \psi = \sum_{n=1}^{N} \xi_t^K \cdot \xi_t^K.$$

Since the wavelet coefficients corresponding to the signal are enhanced in the new detection signal $\zeta_t$ and the local maxima (minima) in $\zeta_t$ can thus be accurately identified by applying a simple scheme of thresholding for the decision making stage.

To perform decision making for detecting QRS complexes, an interval-dependent threshold scheme may be applied to the new detection signal. Assume a detection threshold is $\gamma$ and is calculated in each interval between two consecutive QRS and updated once for every interval. To determine $\gamma$, the standard deviation of $\zeta_t$ may be computed as:

$$\sigma(\zeta_t) = \sqrt{\frac{1}{N} \sum_{i=1}^{N} (x_i - \bar{x}_i)^2}, \, x_i = \zeta_t(i) \tag{47}$$

where N is the number of samples. The standard deviation $\sigma(\zeta_t)$ may be updated every N=1024 samples and the mean value $\zeta_t$ is almost zero per every 1024 samples. Therefore, the equation (47) may be simplified as:

$$\sigma(\zeta_t) = \sqrt{\frac{1}{N} \sum_{i=1}^{N} (x_i)^2}, \, x_i = \zeta_t(i) \tag{48}$$

The detection threshold may be set as $$\gamma = c \cdot [\sigma(\zeta_t)] \tag{49}$$

where constant c is used to adjust the threshold $\gamma$ imposed on $\zeta_t$ and threshold scheme can then be formulated as $$\Phi = \begin{cases} 1 & \zeta_t \geq \gamma \\ 0 & \zeta_t < \gamma \end{cases} \tag{50}$$

$\Phi$ is the vector that contains the site of R peak points. The constant c is adjustable to achieve good detection accuracy.

Implementing the algorithm outlined by the equations (43) to (50), involves considering not only issues such as complexity that directly affect power consumption, but also issues such as available concurrency that indirectly affect power by determining how effectively the algorithm can be implemented on a low-power architecture.

The complexity of an algorithm can be measured in several ways. One measure of complexity is the instruction or operation count. One dominate power consumption in digital CMOS circuits is the switching power dissipation which is given by $$P_{switchin} = \alpha \cdot C_l \cdot V_{DD}^2 \cdot f_{clk} \tag{51}$$

The switching power dissipation depends on four parameters. The switching activity factor $\alpha$, the load capacitance $C_L$, the supply voltage $V_{DD}$ and the clock frequency $f_{clk}$. To minimize power consumption, known systems use low power techniques at both architecture level and logic level have been applied. Typically, the decisions made at the highest levels (architecture and system) will have a dramatic impact on power than those made at a lower level (e.g. gate or circuit). Specifically, they include sharing hardware resources, and clockless datapath of the functional unit.

Returning to FIG. 14, various embodiments provide a low power consumption device by implementing the algorithm outlined by the equations (43) to (50) as follows.

In FIG. 14, various embodiments efficiently implement DYWT through low-pass ($H_1$, $H_2$, $H_3$ and $H_4$) and high-pass ($G_1$, $G_2$, $G_3$, $G_4$) filters independently using folding technique which take advantage of coefficient symmetry to reduce the number of multiplications per output sample. Since the data input to high-pass ($G_1$, $G_2$, $G_3$, $G_4$) and low-pass ($H_1$, $H_2$, $H_3$ and $H_4$) filters are the same at each scale level, the delay elements D can be shared to minimize the hardware cost. The number of delay elements D is increased every level by $[2^{(j-1)}-1]$ since the number of zero coefficients are added between two non-zero coefficients (S. Mallat, and S. Zhong, "Characterization of signals from multiscale edges," *IEEE* Trans. Pattern Analysis and Machine Intelligence, vol. 14, pp. 710-732, 1992). The total hardware cost of DYWT up to level 4 with this architecture is 12 multiplications, 16 additions and 45 delay elements. In order to further optimize the hardware complexity and power consumption, the coefficient multiplier may be replaced by a small number of add/subtract-shift operations.

The high-pass coefficients at scale levels 1, 2 and 3 (i.e., $W_2^1 f(n)$, $W_2^2 f(n)$ and $W_2^2 f(n)$) may be multiplied together to enhance important features while weakening noise. As discussed earlier, the power of $\xi_t^K$ may be rescaled to that of $W_2^j f$ by $\chi$ and $\psi$ to get a new normalized detection signal $\zeta_r$. The rescaling factor $\chi$ and $\psi$ may be updated every 1024 samples so that divider circuitry which has the higher hardware cost can be replaced by simple right-shift 10 bits. Therefore, the new detection signal $\zeta_r$ may be updated every 1024 samples and compared with the threshold generated to identify the location of R-peak.

The threshold generation stage calculates the dynamic threshold $\gamma$ as in equation (49) by multiplying standard deviation of $\zeta_r$ and constant c. The 8-bit width of $\zeta_r$ is multiplied with each other and accumulated into a special 16-bit register without facing overflow issue. The contents of the special register is divided by 1024 (right-shift 10-bits), square-rooting to get a standard deviation of $\zeta_r$. The value of $\zeta_r$ is updated at every 1024 samples. The QRS detection threshold $\gamma$ is evaluated by multiplying constant c. Instead of using a multi-bit comparator, a subtractor circuit may be used to calculate the difference between $\zeta_r$ and $\gamma$ and check the MSB of the subtractor output to locate the positions of R peak. Each non-zero pulse indicating the position of the QRS starts when $\zeta_r$ exceeds $\gamma$.

Figure 15:
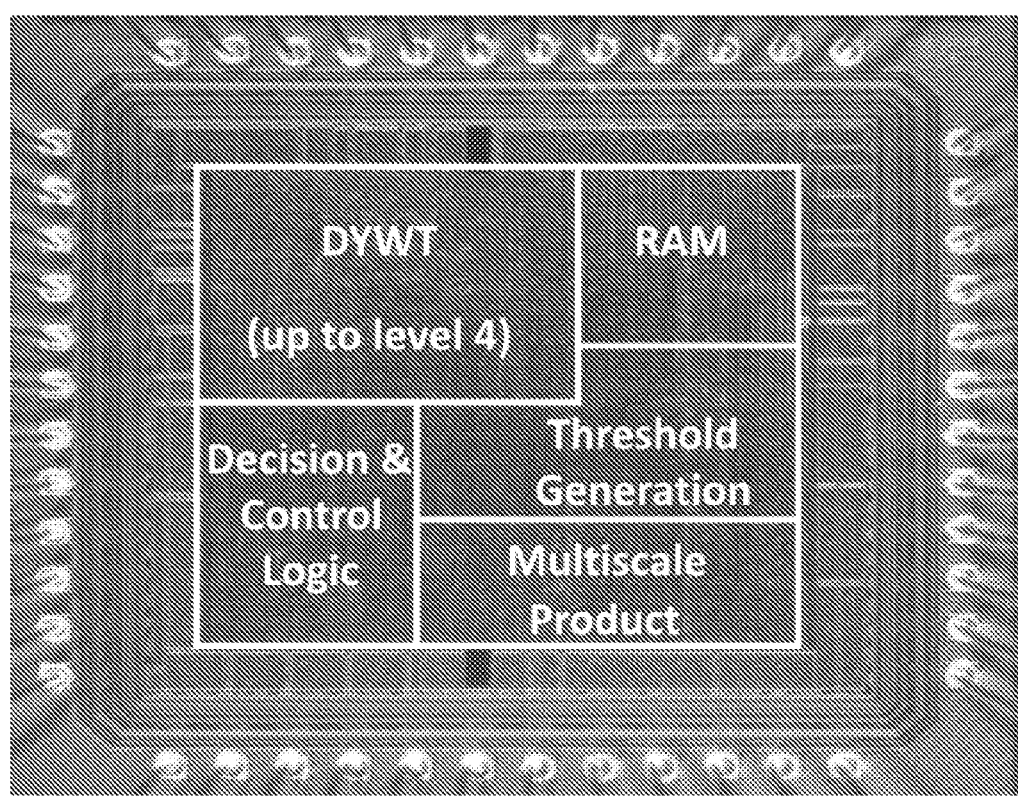
FIG. 15 shows a die photo of a fabricated electrocardiogram signal processing system according to an embodiment.

FIG. 15 shows a die photo of an electrocardiogram signal processing system, having the dyadic wavelet transformation architecture 1400 of FIG. 14, fabricated using Chartered Semiconductor Manufacturing Technology (CHRT) 0.18 µm CMOS technology.

V Advantages of Various Embodiments

Various embodiments allow long-term monitoring and analysis of electrocardiogram (ECG) signals, which is useful for patients who suffer cardio-vascular diseases, so that the doctors can continuously monitor their cardio status in real-time. Various embodiments provide a real-time integrated multi-functional digital ECG signal processing ASIC with minimized area and ultra-low power. This chip of various embodiments can analyze a digitalized ECG signal in a sensor node. Combined with a wireless transceiver (not shown), only the necessary and important analyzed cardio information are wirelessly transmit to healthcare equipments, and thus the sensor node can greatly reduce transmission data rate and power consumption.

Multi-functional: Various embodiments provide a real-time integrated ASIC implementation scheme for ECG signal processing and analysis, which can realize multiple functions: 1). Real-time high-frequency noise suppression and adaptive threshold based QRS detection; 2). Adaptive ECG artificial baseline drifting removal; 3). Real-time HBR prediction/classification; 4). Real-time clean ECG reconstruction. All the functions are based on the intrinsic wavelet transform algorithm. Further, various embodiments can process not only ECG signals, but also other bio-medical signals such as electroencephalography (EEG), electromyography (EMG).

Hardware efficient: All the multiple functions of various embodiments take advantage of the properties of WT. Therefore, the hardware implementation of each function can be shared, resulting in hardware efficient. Based on the property of WT, various embodiments provide a hardware efficient WT decomposition and reconstruction ASIC implementation scheme. Various embodiments apply SRAM to realize FIR filtering. Compared with the conventional scheme using the shift registers, various embodiments reduce hardware cost by about 50%.

Power efficient: The ECG signal processing and analysis scheme used by various embodiments is intrinsic integrated and realizes multiple functions based on the generic WT algorithm. This reusable signal processing scheme is power efficient. The proposed SRAM based WT decomposition and reconstruction ASIC implementation can uses less power as compared with the conventional scheme using shift registers. Clock gating also further reduces the power consumption.

Suitable for long-term monitoring: The ASIC implementation scheme provided by various embodiments allow for long-term cardiac monitoring. The hardware size is quite small, and multiple functions can be realized. Therefore, various embodiments provide an electrocardiogram signal processing system that is very convenient and comfortable for patients to use.

Previous known systems realize different functions using different types of signal processing algorithms. However, the electrocardiogram signal processing system of various embodiments use one generic WT signal processing platform to realize multiple functions. Various embodiments provide an area/power efficient non-downsampling WT ASIC structure for performing generic WT signal processing, capable of realising the following multiple functions:

1. WT based data compression scheme: Various embodiments provide a computational efficient data compression scheme based on the properties of WT. This data compression scheme can be applied on the DHPF outputs of scales 5~8 without distortion. The data compression scheme may be implemented in hardware efficiently and does not need to use multiplication circuits.
2. WT based baseline drift removal scheme: Following WT decomposition, various embodiments use a WT based baseline drift removal scheme to remove DLPF output of scale 8, which contains the most significant low-frequency components. An automatic decision scheme determines whether additional HPF is required, and how many stages of HPF is necessary, for saving power and minimizing the loss of useful ECG information.
3. Adaptive power-efficient Denoising and QRS detection algorithm: Various embodiments use a real-time WT-based ECG QRS detection scheme, which utilizes the wavelet multiscale analysis scheme to suppress high frequency noise and sum denoised outputs of DHPF to accurately detect QRS peaks.
4. HBR prediction and classification scheme for individual status of different patient: Various embodiments provide HBR prediction and classification using an adaptive prediction algorithm. Two different forgetting factors are adopted to obtain long-term and short-term HBR prediction. The dual-threshold can be set according to the long-term HBR prediction to classify tachycardia and bradycardia. The classification scheme used by various embodiments is more accurate than known systems that use a fixed decision threshold, because the baseline of individual status for different patients is taken into consideration.

VI Test and Experiment Results

Figure 16:
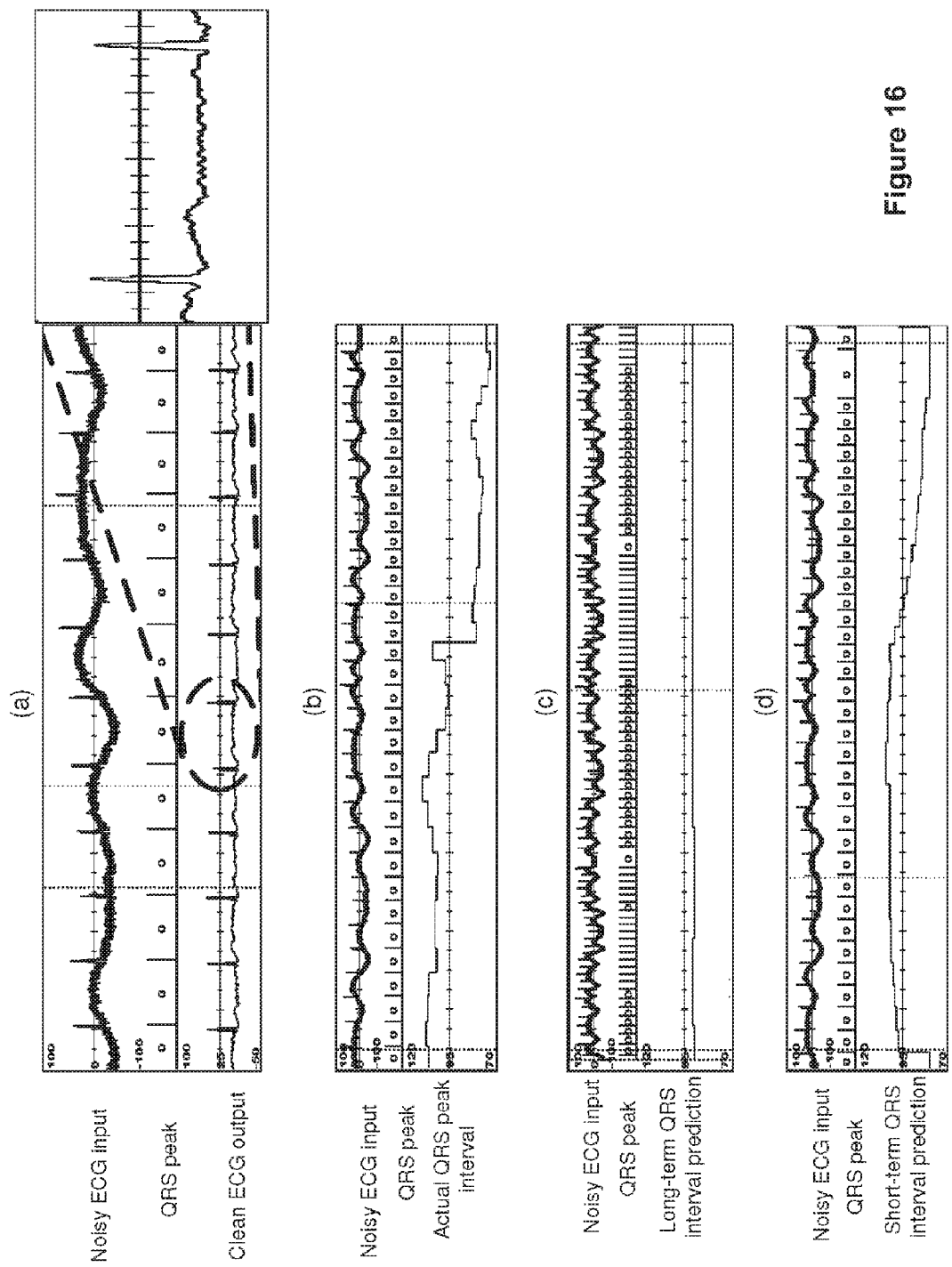
FIG. 16 illustrates measurement results of the chip of FIG. 10B.

FIGS. 16A to 16D illustrate measurement results of the chip of FIG. 10B. The original noisy ECG signals is generated by adding additive white Gaussian noise (AWGN) with SNR=5 dB and artificial baseline on the acquired smooth ECG with 1 kHz sampling rate. The baseline was generated by combining three sine waves with frequencies 0.1, 0.5 and 0.7, respectively. The measured clean ECG is shown in FIG. 16A; the actual QRS interval is shown in FIG. 16B, and the long-term/short-term QRS intervals prediction are illustrated in FIGS. 16C and 16D respectively.

FIGS. 17A to 17D show simulation results of the chip, using Matlab, of FIG. 13 to ECG excerpts from the MIT-BIH Arrhythmia database of Massachusetts Inst. Technolo., Cambridge. Mass., selected to illustrate the robustness of the detector dealing with muscular noise, baseline wandering, different forms of premature mature ventricular contractions (PVCs) and changes in the QRS morphology. The Figures show the performance of the QRS complex detector of the chip of FIG. 13 dealing with different kinds of noise and morphology changes for (FIG. 17A) normal beat in the presence of (ventricular contractions) PVC, (FIG. 17B) different morphologies, (FIG. 17C) moving artifact, and (FIG. 17D) muscular noise.

Figure 17A:
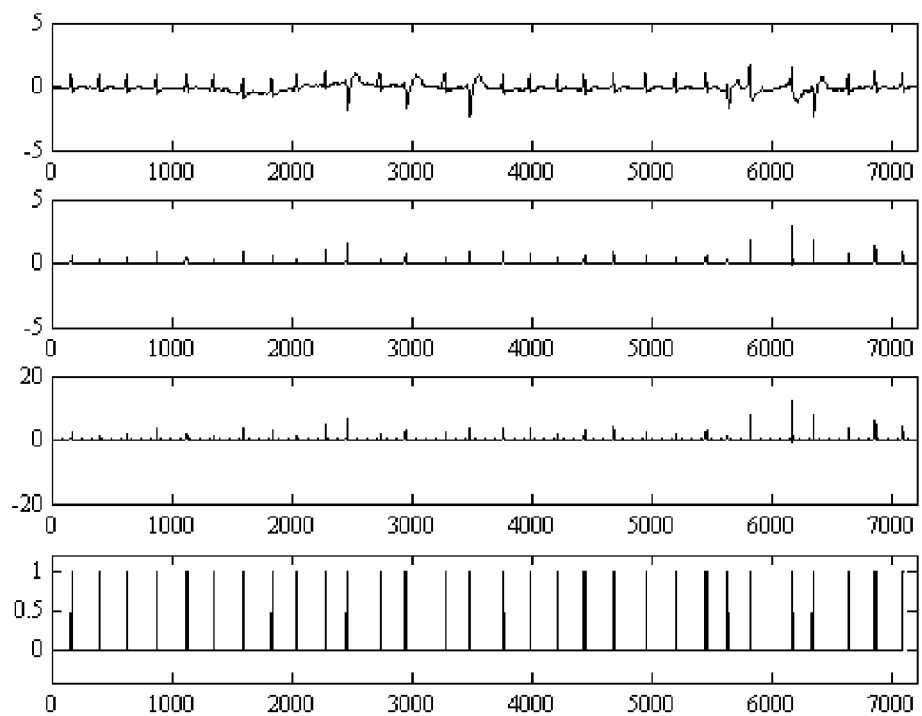
FIGS. 17A to 17D show the performance of the QRS complex detector of the chip of FIG. 13.
Figure 17B:
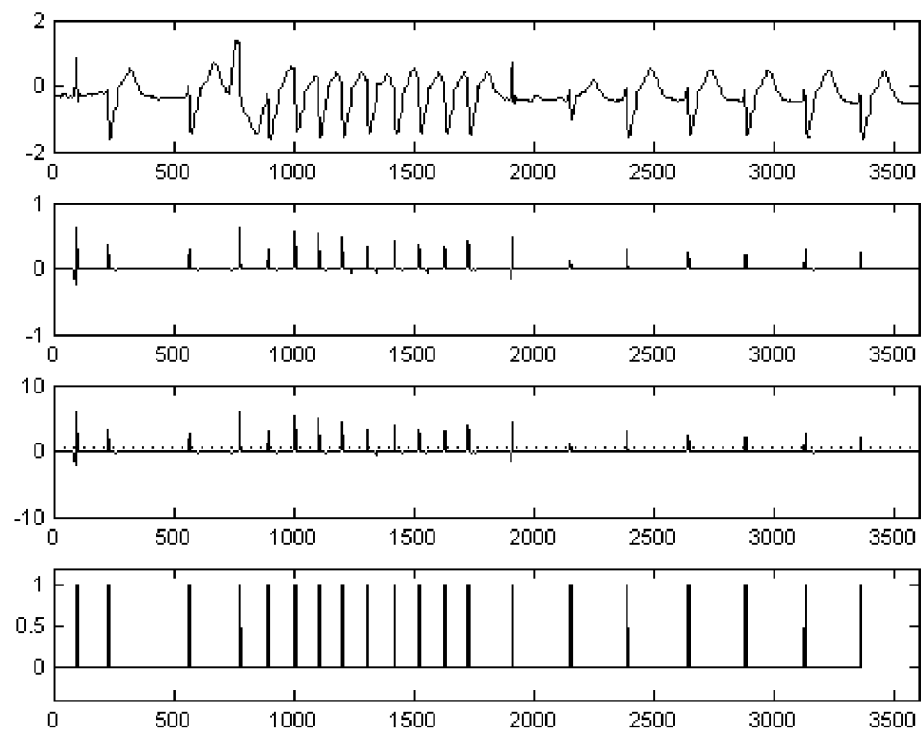
Figure 17C:
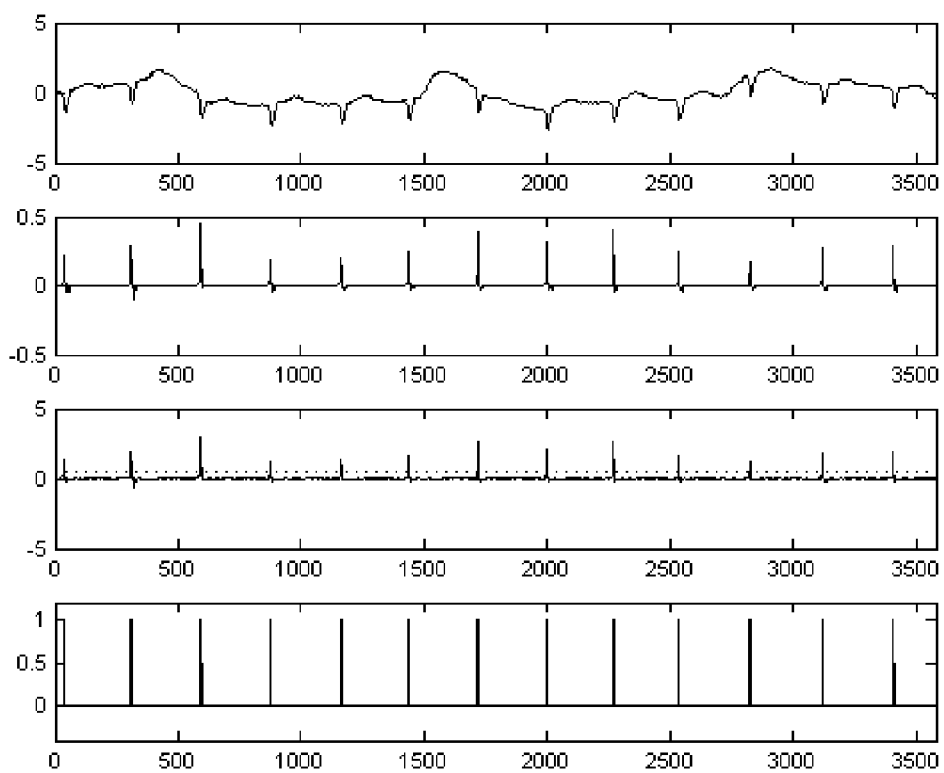
Figure 17D:
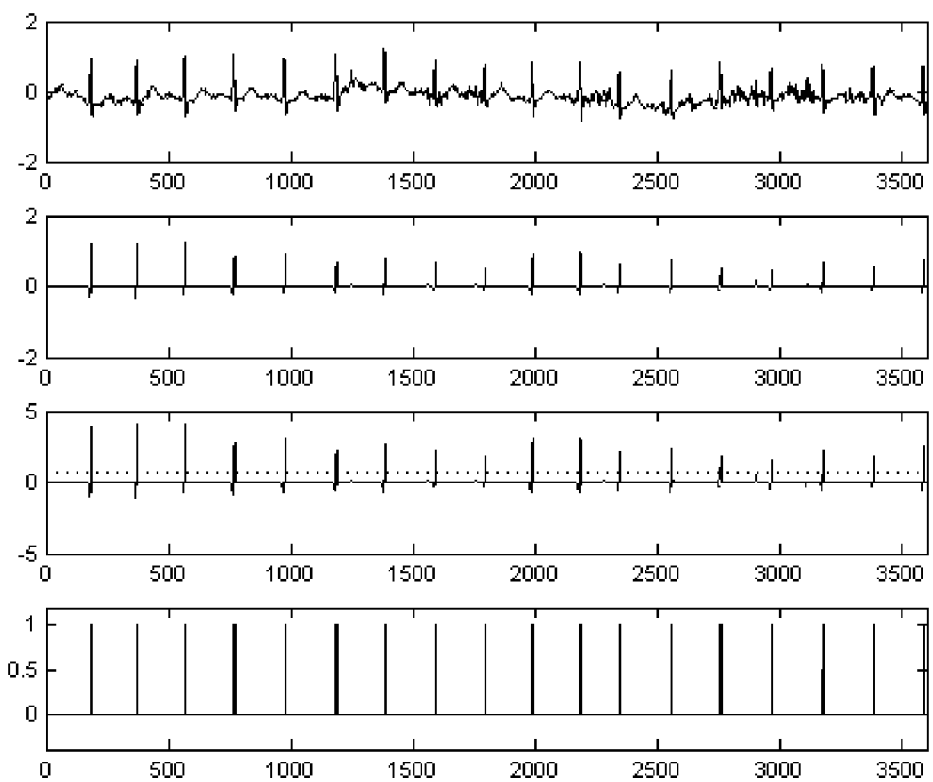

FIG. 18 shows table I summarises obtained QRS detection results of the chip of FIG. 13 for 48 one and half-hour recordings using ECG data records available from the MIT/BIH database of Massachusetts Inst. Technolo., Cambridge. Mass. The database contains 48 half-hour recordings, each of length 650,000 samples, which has following specifications: sampling rate is 360 Hz, resolution is 11 bit, and bit rate is 360 bps. Two benchmark parameters are used to evaluate the performance of the chip of FIG. 13. The sensitivity and positive predictivity of the chip of FIG. 13 is computed by $$Se(\%) = \frac{TP}{TP+FN} \quad (52)$$

$$+P(\%) = \frac{TP}{TP+FP} \quad (53)$$

where TP is the number of true positives detections which means correctly detected beats. False positive (FP) is the number of false positives detection and false Negative (FN) is the number of missed (not detected) beats. The sensitivity Se reports the percentage of true beats that were correctly detected by the algorithm used by the chip of FIG. 13. The positive predicitivty +P reports the percentage of beat detections which were in real true beats. Table I summarizes the accuracy analysis of the proposed QRS detection algorithm for each half-hour ECG recording in the database. Record 105 was more noisy than the others; Record 108 had unusually high and sharp P waves; Record 203 had a great number of QRS complexes with multiform ventricular arrhythmia; records 207 and 208 had multiform premature ventricular contractions and record 222 had several non-QRS waves with highly unusual morphologies. The algorithm used by the chip of FIG. 13 was robust facing up to baseline drift and artifacts. In addition, the algorithm used by the chip of FIG. 13 could analyze special beat morphologies, for instance, premature ventricular contractions with negative QRS-waves (FIG. 17B). However, the rigidness of proposed threshold and DYWT multiscale product scheme produces false detection, especially on PVC sequences and aberrated atrial premature beat with very low amplitude. In particular, detection performance on record 208 suffered from nondetected (FN) beats, mostly very nondetected PVCs have low amplitude and occur between two normal high amplitude beats. In such conditions, these beats do not exceed the detection threshold level, but there is no search back. The nondetected (FN) beats on record 201 and 217 are mainly due to low amplitude aberrated atrial premature beat and pace maker fusion beats. Since QRS amplitude and morphology may change drastically during course of just a few seconds, an adaptive threshold approach can be applied in order to improve the performance. Based on the equations (52) and (53), values of Se=99.54% and +P=99.89% were obtained.

Figure 19:
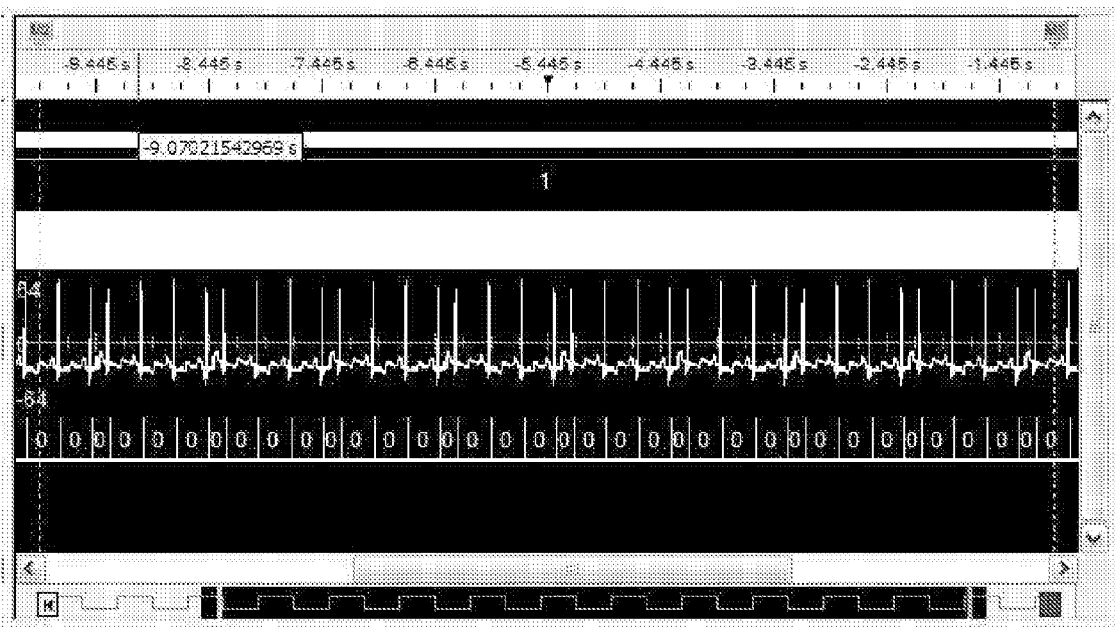
FIG. 19 shows test results, using Agilent Logic Analyzer, of QRS detection for the chip of FIG. 13.

FIG. 19 shows results, using Agilent Logic Analyzer, of QRS detection for the chip of FIG. 13 tested on PCB with 48-pin DIP package. The actual results show good concurrence with simulation results. The results of FIGS. 17 to 19 show that the chip, fabricated in accordance with various embodiments, is well-suited for real time biomedical applications where power constraint is critical.

Figure 20:
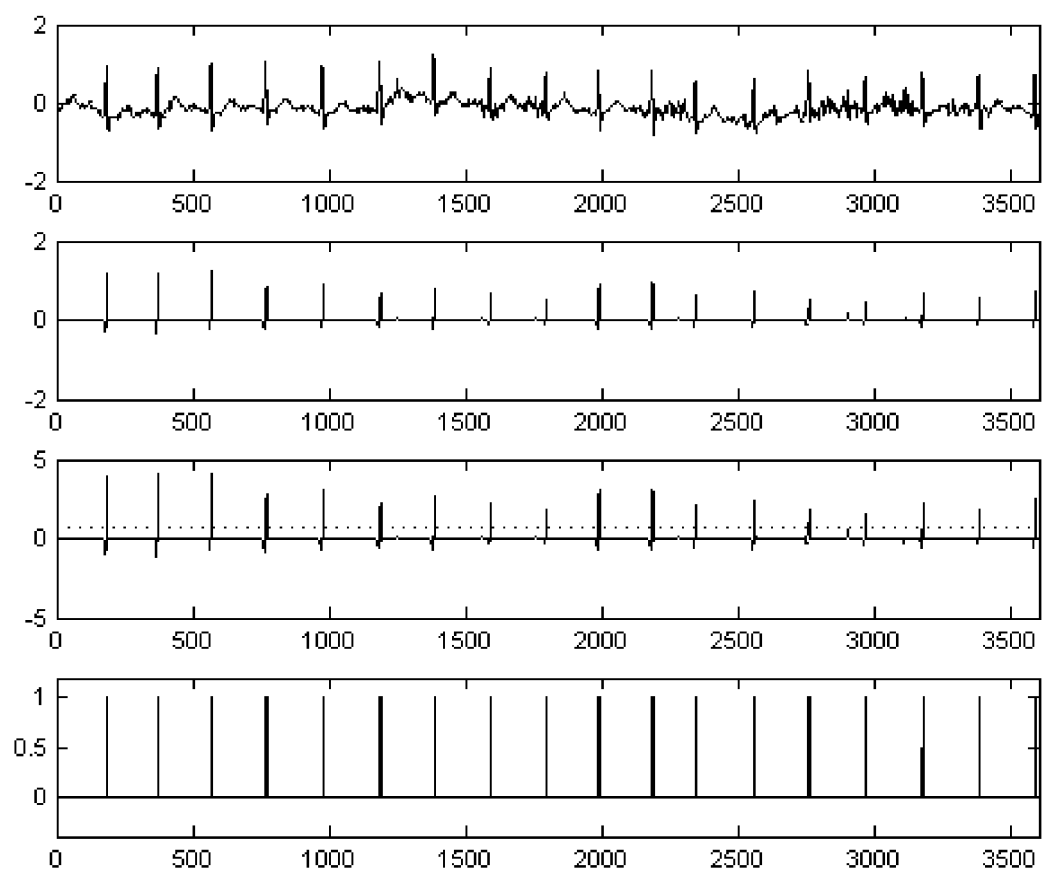
FIG. 20 shows the performance of the chip of FIG. 15.

FIG. 20 shows the performance of the chip of FIG. 15, as implemented in Matlab, to detect QRS complex having muscular noise. Individual detection parameters were set to give optimal QRS complex detection performance in terms of minimum number of missed and falsely detected QRS complexes.

For the chip of FIG. 15, further simulation were carried out using 48 one and half-hour recordings from ECG data records of the MIT-BIH database of Massachusetts Inst. Technolo., Cambridge. Mass. Two benchmark parameters were used to evaluate the performance of detection algorithm used by the chip of FIG. 15. The sensitivity and positive predictivity of the beat detection algorithm were computed by $$Se(\%) = \frac{TP}{TP+FN} \quad (54)$$

$$+P(\%) = \frac{TP}{TP+FP} \quad (55)$$

where TP is the number of true positive detections which means correctly detected beats. FP is the number of false positive detection and FN is the number of missed (not detected) beats. The sensitivity Se reports the percentage of true beats that were correctly detected by the algorithm. The positive predictivity +P reports the percentage of beat detections which were in real true beats. The chip can achieve Se=99.54% and +P=99.89%.

Figure 21:
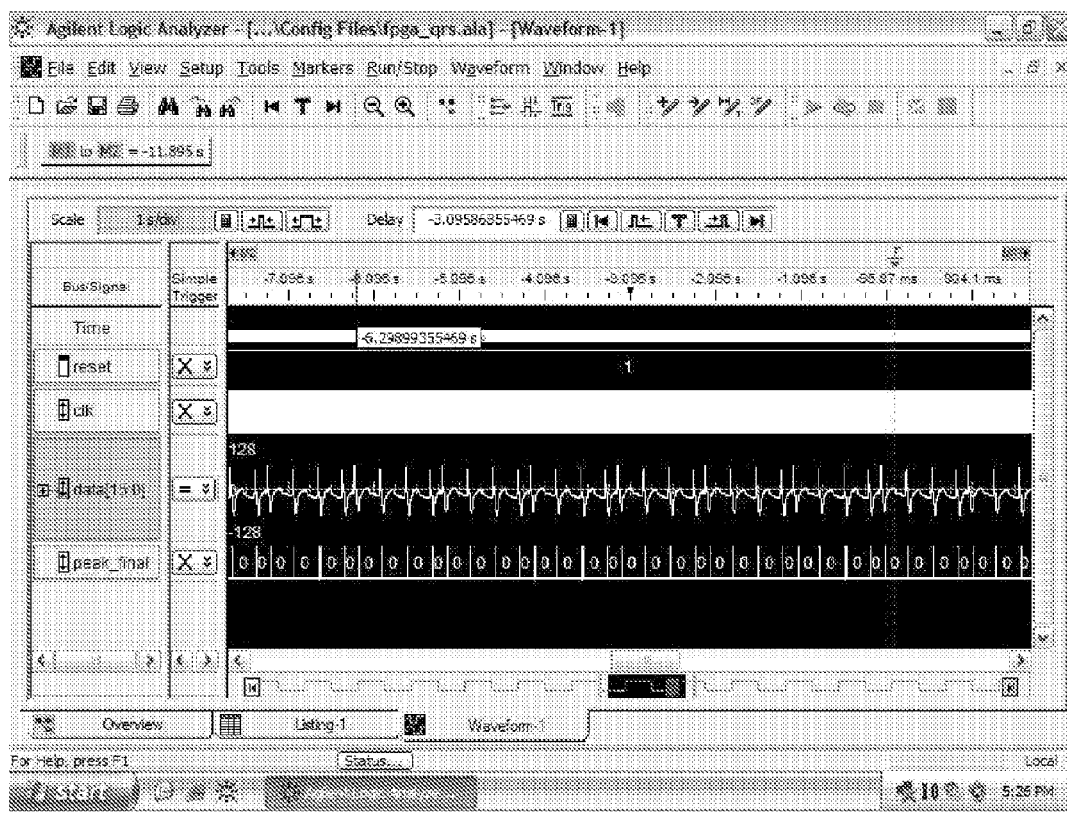
FIG. 21 shows test results, using Agilent Logic Analyzer, of QRS detection for the chip of FIG. 15.

FIG. 21 shows test results, using Agilent Logic Analyzer, of QRS detection for the chip of FIG. 15. The results of FIGS. 20 and 21 show that the chip, fabricated in accordance with various embodiments, is well-suited for real time biomedical applications where power constraint is critical.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An electrocardiogram signal processing system comprising:
   a wavelet transformation unit comprising a plurality of outputs, each output being connected to one of a plurality of scales, wherein the wavelet transformation unit is adapted to transform an input electrocardiogram signal into a set of wavelets, each wavelet being output to one of the scales;
   a plurality of signal processing blocks, each of the signal processing blocks coupled to a respective output of the wavelet transformation unit and configured to receive and process the wavelet from the respective output, wherein the signal processing blocks provide processing functions which differ from one another;
   wherein the scales comprise a first scale, a second scale, a third scale, a fourth scale, a fifth scale, a sixth scale, a seventh scale, and an eighth scale;
   wherein each scale corresponds to a pre-determined bandwidth;
   wherein the signal processing blocks comprise an electrocardiogram signal reconstruction block;

wherein the electrocardiogram signal reconstruction block further comprises:
a first reconstruction block for the fifth to the eighth scales;
a second reconstruction block for the first to the fourth scales; and
a third reconstruction block for the first to the eighth scales;
wherein the first reconstruction block outputs synchronized signals belonging to high-pass filtered components of the fifth to the eighth scales; the second reconstruction block outputs synchronized signals belonging to high-pass filtered components of the first to the fourth scales; and the third reconstruction block outputs signals belonging to low-pass filtered components of the first to the seventh scales.

2. The system of claim 1, wherein each scale has a different bandwidth, wherein the wavelet output to one of the scales is derived from the wavelet output to an earlier scale.

3. The system of claim 2, wherein the number of scales is at least eight, the scales having 3 dB bandwidths of around 250 to 500 Hz; 72 to 234 Hz; 32 to 108 Hz; 16 to 54 Hz; 8 to 26 Hz; 4 to 13 Hz; 2 to 6.5 Hz; and 1 to 3.25 Hz for the first to the eighth scales respectively, when the sampling rate of the input signal is 1 kHz.

4. The system of claim 1, wherein the wavelet transformation unit comprises a plurality of low pass filters and a plurality of high pass filters.

5. The system of claim 4, wherein the low pass filter for the first scale is given by the expression $$l_{D,1}(k) = \frac{1}{8}\{\delta(k+2) + 3\delta(k+1) + 3\delta(k) + \delta(k-1)\}$$

and the high pass filter for the first scale is given by the expression $$h_{D,1}(k) = 2\{\delta(k+1) - \delta(k)\},$$

wherein $\delta(k)$ is the Kronecker delta function and for scale numbers $n>1, l_{D,n}(k)$ and $h_{D,n}(k)$ are obtained by inserting $2^{n-1}-1$ zeros between each of the non-zero coefficients of $l_{D,1}(k)$ and $h_{D,1}(k)$.

6. The system of claim 4, wherein the low pass filters and the high pass filters have a cascaded arrangement, wherein an output of at least one of the low pass filters is coupled to an input of at least one of the high pass filters.

7. The system of claim 4, wherein the wavelet transformation unit comprises a first memory array to achieve delay, the first memory array coupled to the last low pass filter of the cascaded chain of high pass filters and low pass filters.

8. The system of claim 1, wherein the signal processing blocks comprise at least one wavelet denoising unit to suppress high frequency noise.

9. The system of claim 8, wherein each of the at least one wavelet denoising unit is coupled to one of the respective outputs of the wavelet transforming unit emitting wavelets coupled to the first three scales and wherein the suppressed high frequency noise falls in a range of above 32 Hz.

10. The system of claim 8, wherein the signal processing blocks comprise a QRS detection unit, the QRS detection unit coupled to the output of the at least one wavelet denoising unit and the output of the wavelet transforming unit emitting wavelets belonging to the fourth scale.

11. The system of claim 10, wherein the QRS detection unit comprises a wavelet summation unit to sum the denoised wavelets from the at least one wavelet denoising unit and the wavelets from the wavelet transforming unit, wherein QRS peaks are detected when the summed wavelets exceed an adaptive threshold value.

12. The system of claim 11 wherein the QRS detection unit is realized using any of a Field Programmable Gate Array (FPGA), Application Specific Integrated Circuits (ASIC) or software implemented; the wavelet summation unit comprising an adder; and the QRS peaks are detected using a subtractor and multiplexer.

13. The system of claim 11, wherein the adaptive threshold value is derived from a standard deviation of a number of sampled summed wavelets.

14. The system of claim 10, further comprising a heart beat rate (HBR) analysis unit, the HBR analysis unit coupled to an output of the QRS detection unit.

15. The system of claim 14, wherein the HBR analysis unit comprises a counter; two multiplication blocks; an adder and a delay block, wherein the HBR analysis unit is realized by a Field Programmable Gate Array (FPGA), Application Specific Integrated Circuits (ASIC) or software implemented.

16. The system of claim 14, wherein the HBR analysis unit is adapted to predict QRS peak intervals based on a forward prediction algorithm.

17. The system of claim 14, wherein the forward prediction algorithm is based on summing previous QRS peak intervals weighted with a forgetting factor, the forgetting factor determining the number of previous QRS peak intervals included for HBR analysis.

18. The system of claim 1, wherein the first reconstruction block, the second reconstruction block and the third reconstruction block comprise shift registers to achieve delay.

19. The system of claim 1, wherein the first reconstruction block, the second reconstruction block and the third reconstruction block comprise memory arrays to achieve delay for both filtering and synchronization.

20. The system of claim 19, wherein SRAM is used for the memory arrays.

21. The system of claim 1, wherein the output of the first to the third reconstruction blocks is a reconstructed electrocardiogram signal.

22. The system of claim 1, wherein the electrocardiogram signal reconstruction block processes wavelets belonging to the first to the eighth scales.

23. The system of claim 1, wherein the second reconstruction block is coupled to an output of a wavelet denoising unit to receive denoised wavelets belonging to the first to the third scales.

24. The system of claim 1, the system further comprising a data compression block, the data compression block receiving wavelets of the fifth to the eighth scales, wherein an output of the data compression block is coupled to the input of the first reconstruction block.

25. The system of claim 24, wherein the data compression block is realized using finite-impulse-response filters with zeros and infinite-impulse-response filters with poles, wherein the zeros of the finite-impulse-response filters compensate the poles of the infinite-impulse-response filters.

26. The system of claim 1, wherein the signal processing blocks comprises a baseline drift removal unit, the baseline drift removal unit coupled to the respective output of the wavelet transforming unit emitting wavelets belonging to the seventh and the eighth scales.

27. The system of claim 26, wherein the baseline drift removal block is realized by an adaptive cascaded filter arrangement, the cascaded filter arrangement comprising at least one filter stage.

28. The system of claim 27, wherein the adaptive cascaded filter arrangement comprises chebyshev IIR filters.

29. The system of claim 27, wherein the adaptive cascaded filter arrangement automatically switches off filter stages unnecessary for performing baseline drift removal.

30. The system of claim 29, wherein the unnecessary filter stages are those larger than a filter stage in which the difference in the output value of the filter stage and an output value of the largest filter stage is smaller than a specified threshold.

* * * * *

UNITED STATES PATENT AND TRADEMARK OFFICE
CERTIFICATE OF CORRECTION

PATENT NO. : 8,725,238 B2
APPLICATION NO. : 12/878800
DATED : May 13, 2014
INVENTOR(S) : Xin Liu et al.

Page 1 of 1

It is certified that error appears in the above-identified patent and that said Letters Patent is hereby corrected as shown below:

In the Specification

Column 16, line 67, "... for calculating A and ..." should be --... for calculating $A_i$ and ...--.

Signed and Sealed this
Seventh Day of October, 2014

Michelle K. Lee
*Deputy Director of the United States Patent and Trademark Office*